United States Patent
Zhang et al.

(10) Patent No.: US 8,239,020 B2
(45) Date of Patent: Aug. 7, 2012

(54) IMPLANTABLE MEDICAL DEVICE SENSING WIRELESS ECG AS SUBSTITUTE FOR INTRACARDIAC ELECTROGRAM

(75) Inventors: Yi Zhang, Blaine, MN (US); Aaron McCabe, Minneapolis, MN (US); David J. Yonce, Fridley, MN (US); Julie Thompson, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 646 days.

(21) Appl. No.: 11/693,110

(22) Filed: Mar. 29, 2007

(65) Prior Publication Data
US 2007/0167849 A1   Jul. 19, 2007

Related U.S. Application Data

(62) Division of application No. 10/975,166, filed on Oct. 28, 2004, now Pat. No. 7,212,849.

(51) Int. Cl.
*A61N 1/372* (2006.01)
(52) U.S. Cl. .............. 607/9; 607/17; 607/18; 600/509
(58) Field of Classification Search ............ 600/509, 600/515, 518, 508, 517; 607/5, 14, 18, 4, 607/9, 17
See application file for complete search history.

(56) References Cited

U.S. PATENT DOCUMENTS

| | | | |
|---|---|---|---|
| 4,088,139 A | 5/1978 | Auerbach | |
| 4,333,470 A | 6/1982 | Barthel | |
| 4,531,527 A | 7/1985 | Reinhold, Jr. et al. | |
| 4,539,999 A | 9/1985 | Mans | |
| 4,562,841 A | 1/1986 | Brockway et al. | |
| 4,585,004 A | 4/1986 | Brownlee | |
| 4,589,420 A | 5/1986 | Adams et al. | |
| RE32,378 E | 3/1987 | Barthel | |
| 4,884,345 A | 12/1989 | Long | |
| 4,924,875 A | 5/1990 | Chamoun | |
| 5,000,189 A | 3/1991 | Throne et al. | |
| 5,002,052 A | 3/1991 | Haluska | |
| 5,014,698 A | 5/1991 | Cohen | |
| 5,107,850 A | 4/1992 | Olive | |
| 5,113,869 A | 5/1992 | Nappholz et al. | |
| 5,127,401 A | 7/1992 | Grevious et al. | |
| 5,139,028 A | 8/1992 | Steinhaus et al. | |
| 5,156,148 A | 10/1992 | Cohen | |

(Continued)

FOREIGN PATENT DOCUMENTS
EP   253505   1/1988
(Continued)

OTHER PUBLICATIONS

"International Search Report and Written Opinion for Application No. PCT/US2005/035057, date mailed Feb. 1, 2006", 17 Pages.

(Continued)

*Primary Examiner* — Carl H Layno
*Assistant Examiner* — Pamela M Bays
(74) *Attorney, Agent, or Firm* — Schwegman, Lundberg & Woessner, P.A.

(57) ABSTRACT

A cardiac rhythm management (CRM) system includes an implantable medical device that senses a wireless electrocardiogram (ECG), which is a signal sensed with implantable electrodes and approximating a surface ECG. In one embodiment, the wireless ECG is sensed as a substitute signal for the intracardiac electrogram when the sensing of the intracardiac electrogram becomes unreliable.

19 Claims, 15 Drawing Sheets

U.S. PATENT DOCUMENTS

| | | | |
|---|---|---|---|
| 5,161,527 A | 11/1992 | Nappholz et al. |
| 5,193,550 A | 3/1993 | Duffin |
| 5,205,283 A | 4/1993 | Olson |
| 5,215,098 A | 6/1993 | Steinhaus et al. |
| 5,217,021 A | 6/1993 | Steinhaus et al. |
| 5,255,186 A | 10/1993 | Steinhaus et al. |
| 5,265,602 A | 11/1993 | Anderson et al. |
| 5,271,411 A | 12/1993 | Ripley et al. |
| 5,273,049 A | 12/1993 | Steinhaus et al. |
| 5,275,621 A | 1/1994 | Mehra |
| 5,292,348 A | 3/1994 | Saumarez et al. |
| 5,312,445 A | 5/1994 | Nappholz et al. |
| 5,313,953 A | 5/1994 | Yomtov et al. |
| 5,324,310 A | 6/1994 | Greeninger et al. |
| 5,331,966 A * | 7/1994 | Bennett et al. ............ 600/508 |
| 5,360,436 A | 11/1994 | Alt et al. |
| 5,366,487 A | 11/1994 | Adams et al. |
| 5,378,775 A | 1/1995 | Shimizu et al. |
| 5,379,775 A | 1/1995 | Kruse |
| 5,379,776 A | 1/1995 | Murphy et al. |
| 5,388,578 A | 2/1995 | Yomtov et al. |
| 5,400,795 A | 3/1995 | Murphy et al. |
| 5,411,031 A | 5/1995 | Yomtov |
| 5,447,524 A | 9/1995 | Alt |
| 5,448,997 A | 9/1995 | Kruse et al. |
| 5,456,261 A | 10/1995 | Luczyk |
| 5,458,623 A | 10/1995 | Lu et al. |
| 5,503,160 A | 4/1996 | Pering et al. |
| 5,509,927 A | 4/1996 | Epstein et al. |
| 5,520,191 A | 5/1996 | Karlsson et al. |
| 5,531,767 A | 7/1996 | Fain |
| 5,620,471 A | 4/1997 | Duncan |
| 5,630,425 A | 5/1997 | Panescu |
| 5,634,468 A | 6/1997 | Platt et al. |
| 5,645,070 A | 7/1997 | Turcott |
| 5,682,900 A | 11/1997 | Arand et al. |
| 5,683,425 A | 11/1997 | Hauptmann |
| 5,712,801 A | 1/1998 | Turcott |
| 5,713,367 A | 2/1998 | Arnold et al. |
| 5,738,105 A | 4/1998 | Kroll |
| 5,766,225 A | 6/1998 | Kramm |
| 5,776,168 A | 7/1998 | Gunderson |
| 5,779,645 A | 7/1998 | Olson et al. |
| 5,792,065 A | 8/1998 | Xue et al. |
| 5,795,303 A | 8/1998 | Swanson et al. |
| 5,817,133 A | 10/1998 | Houben |
| 5,819,741 A | 10/1998 | Karlsson et al. |
| 5,827,197 A | 10/1998 | Bocek et al. |
| 5,848,972 A | 12/1998 | Triedman et al. |
| 5,857,977 A | 1/1999 | Caswell et al. |
| 5,873,897 A | 2/1999 | Armstrong et al. |
| 5,891,170 A | 4/1999 | Nitzsche et al. |
| 5,935,081 A | 8/1999 | Kadhiresan |
| 5,954,662 A | 9/1999 | Swanson et al. |
| 5,978,707 A | 11/1999 | Krig et al. |
| 6,108,578 A | 8/2000 | Bardy et al. |
| 6,134,463 A * | 10/2000 | Wittkampf et al. ........ 600/374 |
| 6,151,524 A | 11/2000 | Krig et al. |
| 6,169,918 B1 | 1/2001 | Haefner et al. |
| 6,178,350 B1 | 1/2001 | Olson et al. |
| 6,179,865 B1 | 1/2001 | Hsu et al. |
| 6,212,428 B1 | 4/2001 | Hsu et al. |
| 6,223,078 B1 | 4/2001 | Marcovecchio |
| 6,230,055 B1 | 5/2001 | Sun et al. |
| 6,230,059 B1 | 5/2001 | Duffin |
| 6,266,554 B1 | 7/2001 | Hsu et al. |
| 6,275,732 B1 | 8/2001 | Hsu et al. |
| 6,308,095 B1 | 10/2001 | Hsu et al. |
| 6,312,388 B1 | 11/2001 | Marcovecchio et al. |
| 6,317,632 B1 | 11/2001 | Krig et al. |
| 6,334,071 B1 * | 12/2001 | Lu ................................. 607/20 |
| 6,405,083 B1 | 6/2002 | Rockwell et al. |
| 6,430,435 B1 | 8/2002 | Hsu et al. |
| 6,434,417 B1 | 8/2002 | Lovett |
| 6,449,503 B1 | 9/2002 | Hsu |
| 6,456,871 B1 | 9/2002 | Hsu et al. |
| 6,477,404 B1 | 11/2002 | Yonce et al. |
| 6,480,733 B1 | 11/2002 | Turcott |
| 6,484,055 B1 | 11/2002 | Marcovecchio |
| 6,493,579 B1 | 12/2002 | Gilkerson et al. |
| 6,505,067 B1 | 1/2003 | Lee et al. |
| 6,512,940 B1 | 1/2003 | Brabec et al. |
| 6,522,917 B1 | 2/2003 | Hsu et al. |
| 6,522,925 B1 | 2/2003 | Gilkerson et al. |
| 6,526,313 B2 | 2/2003 | Sweeney et al. |
| 6,658,283 B1 | 12/2003 | Bornzin et al. |
| 6,658,286 B2 | 12/2003 | Seim |
| 6,671,548 B1 | 12/2003 | Mouchawar et al. |
| 6,687,540 B2 | 2/2004 | Marcovecchio |
| 6,708,058 B2 | 3/2004 | Kim et al. |
| 6,728,572 B2 | 4/2004 | Hsu et al. |
| 6,745,068 B2 | 6/2004 | Koyrakh et al. |
| 6,760,615 B2 | 7/2004 | Ferek-Petric |
| 6,766,190 B2 | 7/2004 | Ferek-Petric |
| 6,889,081 B2 | 5/2005 | Hsu |
| 6,959,212 B2 | 10/2005 | Hsu et al. |
| 7,031,764 B2 | 4/2006 | Schwartz et al. |
| 7,039,463 B2 | 5/2006 | Marcovecchio |
| 7,107,093 B2 | 9/2006 | Burnes |
| 7,751,890 B2 | 7/2010 | McCabe et al. |
| 7,991,457 B2 | 8/2011 | Marcovecchio |
| 2002/0002389 A1 | 1/2002 | Bradley et al. |
| 2002/0032469 A1 | 3/2002 | Marcovecchio |
| 2002/0035335 A1 | 3/2002 | Schauerte |
| 2002/0049474 A1 | 4/2002 | Marcovecchio et al. |
| 2002/0065539 A1 * | 5/2002 | Von Arx et al. ............. 607/60 |
| 2002/0072778 A1 | 6/2002 | Guck et al. |
| 2002/0087091 A1 | 7/2002 | Koyrakh et al. |
| 2002/0091333 A1 | 7/2002 | Hsu et al. |
| 2002/0107552 A1 | 8/2002 | Krig et al. |
| 2002/0123768 A1 | 9/2002 | Gilkerson |
| 2002/0123769 A1 | 9/2002 | Panken et al. |
| 2002/0143370 A1 | 10/2002 | Kim |
| 2002/0147407 A1 | 10/2002 | Seim |
| 2002/0147474 A1 | 10/2002 | Seim et al. |
| 2002/0183637 A1 | 12/2002 | Kim et al. |
| 2002/0183639 A1 | 12/2002 | Sweeney et al. |
| 2002/0198461 A1 | 12/2002 | Hsu et al. |
| 2003/0004552 A1 | 1/2003 | Plombon et al. |
| 2003/0050563 A1 | 3/2003 | Suribhotla et al. |
| 2003/0060849 A1 | 3/2003 | Hsu |
| 2003/0069609 A1 | 4/2003 | Thompson |
| 2003/0083586 A1 | 5/2003 | Ferek-Petric |
| 2003/0083587 A1 | 5/2003 | Ferek-Petric |
| 2003/0100923 A1 | 5/2003 | Bjorling et al. |
| 2003/0105491 A1 | 6/2003 | Gilkerson et al. |
| 2003/0109792 A1 | 6/2003 | Hsu et al. |
| 2003/0114889 A1 | 6/2003 | Huvelle et al. |
| 2003/0120316 A1 | 6/2003 | Spinelli et al. |
| 2003/0181818 A1 | 9/2003 | Kim et al. |
| 2003/0208238 A1 | 11/2003 | Weinberg et al. |
| 2004/0015090 A1 | 1/2004 | Sweeney et al. |
| 2004/0093035 A1 | 5/2004 | Schwartz et al. |
| 2004/0116820 A1 | 6/2004 | Daum et al. |
| 2004/0116972 A1 | 6/2004 | Marcovecchio |
| 2004/0127806 A1 | 7/2004 | Sweeney |
| 2004/0176694 A1 | 9/2004 | Kim et al. |
| 2004/0215240 A1 | 10/2004 | Lovett et al. |
| 2004/0230229 A1 | 11/2004 | Lovett et al. |
| 2005/0010257 A1 | 1/2005 | Lincoln et al. |
| 2005/0149134 A1 | 7/2005 | McCabe et al. |
| 2005/0149135 A1 | 7/2005 | Krig et al. |
| 2005/0159781 A1 | 7/2005 | Hsu et al. |
| 2005/0197674 A1 | 9/2005 | McCabe et al. |
| 2005/0256544 A1 | 11/2005 | Thompson |
| 2006/0015148 A1 | 1/2006 | McCabe et al. |
| 2006/0074330 A1 | 4/2006 | Smith et al. |
| 2006/0122527 A1 | 6/2006 | Marcovecchio |

FOREIGN PATENT DOCUMENTS

| | | |
|---|---|---|
| EP | 0308536 A1 | 3/1989 |
| EP | 0360412 | 3/1990 |
| EP | 0401962 | 12/1990 |
| EP | 469817 | 2/1992 |
| EP | 0 506 230 | 9/1992 |
| EP | 0554208 | 8/1993 |
| EP | 0597459 | 5/1994 |

| | | |
|---|---|---|
| EP | 0597459 A2 | 5/1994 |
| EP | 0617980 | 10/1994 |
| EP | 0711531 | 5/1996 |
| EP | 744190 | 11/1996 |
| EP | 0748638 | 12/1996 |
| EP | 0784996 A1 | 7/1997 |
| EP | 0848965 | 6/1998 |
| EP | 0879621 A2 | 11/1998 |
| EP | 919256 | 6/1999 |
| EP | 993842 | 4/2000 |
| EP | 1112756 | 7/2001 |
| WO | WO93/02746 | 2/1993 |
| WO | WO-9401173 A1 | 1/1994 |
| WO | WO-97/39681 | 10/1997 |
| WO | WO-9739799 | 10/1997 |
| WO | WO-9825669 | 6/1998 |
| WO | WO-98/40010 | 9/1998 |
| WO | WO-9848891 | 11/1998 |
| WO | WO 98/53879 | 12/1998 |
| WO | WO-9915232 | 4/1999 |
| WO | WO-0053089 | 9/2000 |
| WO | WO-0059573 | 10/2000 |
| WO | WO-0113993 | 3/2001 |
| WO | WO-0126733 A1 | 4/2001 |
| WO | WO-03047690 | 6/2003 |
| WO | WO-2005089643 A1 | 9/2005 |
| WO | WO-2006020198 A2 | 2/2006 |
| WO | WO-2006020198 A3 | 2/2006 |
| WO | WO-2006049767 A1 | 5/2006 |

OTHER PUBLICATIONS

Chen, Victor T., "Method and Apparatus for Using Atrial Discrimination Algorithms to Determine Optimal Pacing Therapy and Therapy Timing", U.S. Appl. No. 09/712,600, filed Nov. 14, 2000, 34 pgs.

Duru, Firat , et al., "The Potential for Inappropriate Ventricular Tachycardia Confirmation Using the Intracardiac Electrogram (EGM) Width Criterion", *PACE*, vol. 22, 1999, (Jul. 1999),1039-1046.

Grady, Thomas A., et al., "Prognostice Significance of Exercise-Induced Left Bundle-Branch Block", *JAMA*, vol. 279, No. 2, Jan. 14, 1998, 153-156.

Hsu, William , "System and Method for Classifying Tachycardia Arrhythmias Having 1:1 Atrial to Ventricular Rhythms", U.S. Appl. No. 09/417,588, filed Oct. 13, 1999, 39 pgs.

Hughes, Howard C., et al., "The Effects of Electrode Position on the Detection of the Transvenous Cardiac Electrogram", *PACE*, vol. 3. (Nov.-Dec. 1980),651-655.

Kinoshita, Shinji et al., "Transient Disapperance of Complete Right Bundle Branch (BBB) During Exercise", *Journal of Electrocardiology*, vol. 29. No. 3, 1996, (1996),255-256.

Leitch, James , et al., "Feasibility of an implantable arrhythmia monitor", *PACE*, vol. 15, No. 12, (Dec. 1992),2232-5.

Li, Dan , "Method and Apparatus for Rate-Dependent Morphology-Based Cardiac Arrhythmia Classification", U.S. Appl. No. 11/151,567, filed Jun. 13, 2005, 53 pgs.

Mazur, Alexander , "Functional similarity between electrograms recorded from an implantable cardioverter defibrillator emulator and the surface electrocardiogram", *PACE*, vol. 24, (Jan. 2001),34-40.

McCabe, Aaron "Self-Diagnostic Method and System for Implantable Cardiac Device", U.S. Appl. No. 10/890,810, filed Jul. 14, 2004, 18 pgs.

Medtronic, "Marquis DR 7274 Dual Chamber Implantable Cardioverter Defibrillator", Reference Manual,(Feb. 2002),426 pgs.

Morris, Milton M., "Detection of Atrial Arrhythmia for Cardiac Rhythm Management by Implantable Devices", *Journal of Electrocardiology*, vol. 33, (2000),133-139.

Smith, V. , "Systems, Devices and Methods for Tachyarrythmia Discrimination or Therapy Decisions", U.S. Appl. No. 10/897,365, filed Jul. 22, 2004, 38 pgs.

Theres, Heinz , et al., "Electrogram signals recorded from acute and chronic pacemaker implantation sites in pacemaker patie", *PACE*, vol. 21, Part 1, (Jan. 1998),11-17.

Thompson, Julie , "Template Based AV/VA Interval Comparison for the Discrimination of Cardiac Arrhythmia", U.S. Appl. No. 10/844,475, filed May 12, 2004, 33 pgs.

Zhu, D. W., "Electrophysiology, Pacing and Arrhythmia—Pacing Therapy for Atrial Tachyarrhythmias", *Clinical Cardiolony*, 19(9), (1996),737-742.

"U.S. Appl. No. 10/890,810, Final Office Action mailed Feb. 5, 2009", 6 pgs.

"U.S. Appl. No. 10/890,810, Non Final Office Action mailed Oct. 12, 2007", 9 pgs.

"U.S. Appl. No. 10/890,810, Non-Final Office Action mailed Jul. 27, 2009", 7 Pgs.

"U.S. Appl. No. 10/890,810, Non-Final Office Action mailed Aug. 21, 2008", 6 pgs.

"U.S. Appl. No. 10/890,810, Response filed Jan. 14, 2008 to Non-Final Office Action mailed Oct. 12, 2007", 8 pgs.

"U.S. Appl. No. 10/890,810, Response filed May 5, 2009 to Final Office Action mailed Feb. 5, 2009", 8 pgs.

"U.S. Appl. No. 10/890,810, Response filed May 19, 2008 to Restriction Requirement mailed Apr. 18, 2008", 7 pgs.

"U.S. Appl. No. 10/890,810, Response filed Oct. 27, 2009 to Non Final Office Action mailed Jul. 27, 2009", 9 pgs.

"U.S. Appl. No. 10/890,810, Response filed Nov. 20, 2008 to Non Final Office Action mailed Aug. 21, 2008", 9 pgs.

"U.S. Appl. No. 10/890,810, Restriction Requirement mailed Apr. 18, 2008", 5 pgs.

"U.S. Appl. No. 10/975,166, Notice of Allowance mailed Dec. 21, 2006", 17 pgs.

"U.S. Appl. No. 10/975,166, Preliminary Amendment and Examiner Interview Summary filed Dec. 8, 2006", 8 pgs.

"U.S. Appl. No. 10/975,166, Response filed Jul. 7, 2006 to Restriction Requirement mailed Jun. 7, 2006", 20 pgs.

"U.S. Appl. No. 10/975,166, Restriction Requirement mailed Jun. 7, 2006", 9 pgs.

"European Application Serial No. 05800091.0, Communication dated Jun. 18, 2007", 2 pgs.

"European Application Serial No. 05800091.0, Response filed Jul. 26, 2007 to Communication dated Jun. 18, 2007", 18 pgs.

"U.S. Appl. No. 10/890,810, Notice of Allowance mailed Feb. 24, 2010", 4 pgs.

"Japanese Application Serial No. 2007-538936, Office Action dated Jul. 19, 2011", (w/ Partial English Translation), 7 pgs.

U.S. Appl. No. 13/246,400, filed Sep. 27, 2011, Apparatus and Method for Treating Ventricular Tachyarrhythmias.

U.S. Appl. No. 13/288,105, filed Nov. 3, 2011, Wireless ECG in Implantable Devices.

* cited by examiner

IMPLANTABLE MEDICAL DEVICE SENSING WIRELESS ECG AS SUBSTITUTE FOR INTRACARDIAC ELECTROGRAM

CROSS-REFERENCE TO RELATED APPLICATIONS

This application is a division of U.S. patent application Ser. No. 10/975,166, filed on Oct. 28, 2004, now U.S. Pat. No. 7,212,849, the specification of which is incorporated herein by reference.

This application is related to, commonly assigned U.S. patent application Ser. No. 10/897,365, entitled "SYSTEMS, DEVICES, AND METHODS FOR TACHYARRHYTHMIA DISCRIMINATION OR THERAPY DECISIONS," filed on Jul. 22, 2004, now issued as U.S. Pat. No. 7,228,176, U.S. patent application Ser. No. 10/890,810, entitled "SELF-DIAGNOSTIC METHOD AND SYSTEM FOR IMPLANTABLE CARDIAC DEVICE," filed on Jul. 14, 2004, U.S. patent application Ser. No. 10/795,126, entitled "WIRELESS ECG IN IMPLANTABLE DEVICES," filed on Mar. 5, 2004, now issued as U.S. Pat. No. 7,299,086, U.S. patent application Ser. No. 10/746,855, entitled "WIRELESS ECG PACE AVOIDANCE AND DISPLAY METHOD," filed on Dec. 24, 2003, now issued as U.S. Pat. No. 7,277,754, U.S. patent application Ser. No. 10/731,223, entitled "DISCRIMINATION OF SUPRAVENTRICULAR TACHYCARDIA AND VENTRICULAR TACHYCARDIA EVENTS," filed on Dec. 9, 2003, now issued as U.S. Pat. No. 7,039,463, U.S. patent application Ser. No. 10/339,926, entitled "SYSTEM AND METHOD FOR DETECTION ENHANCEMENT PROGRAMMING," filed on Jan. 10, 2003, now abandoned, U.S. patent application Ser. No. 10/291,200, entitled "CARDIAC RHYTHM MANAGEMENT SYSTEMS AND METHODS USING MULTIPLE MORPHOLOGY TEMPLATES FOR DISCRIMINATING BETWEEN RHYTHMS," filed on Nov. 8, 2002, now issued as U.S. Pat. No. 7,031,764, U.S. patent application Ser. No. 10/025,958, entitled "SYSTEM AND METHOD FOR DETECTION ENHANCEMENT PROGRAMMING," filed on Dec. 18, 2001, now issued as U.S. Pat. No. 7,532,931, U.S. patent application Ser. No. 10/008,367, entitled "APPARATUS AND METHOD FOR TREATING VENTRICULAR TACHYARRHYTHMIAS," filed on Nov. 13, 2001, now issued as U.S. Pat. No. 7,113,824, and U.S. patent application Ser. No. 10/014,933, entitled "SYSTEM AND METHOD FOR ARRHYTHMIA DISCRIMINATION," filed on Oct. 22, 2001, now issued as U.S. Pat. No. 6,959,212, which are hereby incorporated by reference in their entirety.

TECHNICAL FIELD

This document generally relates to cardiac rhythm management (CRM) systems and particularly, but not by way of limitation, to such systems providing for detection and classification of cardiac arrhythmias using wireless electrocardiogram (ECG), which is sensed by an implantable device using implantable electrodes and approximates a surface ECG.

BACKGROUND

The heart is the center of a person's circulatory system. It includes a complex electro-mechanical system performing two major pumping functions. The left portions of the heart, including the left atrium (LA) and the left ventricle (LV), draw oxygenated blood from the lungs and pump it to the organs of the body to provide the organs with their metabolic needs for oxygen. The right portions of the heart, including the right atrium (RA) and the right ventricle (RV), draw deoxygenated blood from the organs and pump it into the lungs where the blood gets oxygenated. These mechanical pumping functions are accomplished by contractions of the myocardium (heart muscles). In a heart having a normal electrical system, the sinoatrial node, the heart's natural pacemaker, generates electrical signals, called action potentials, at a rate responsive to the body's metabolic need. The action potentials propagate through an electrical conduction system to various regions of the heart to excite myocardial tissues in these regions. Coordinated delays in the propagations of the action potentials in a normal electrical conduction system cause the various regions of the heart to contract in synchrony such that the pumping functions are performed efficiently. When the electrical system functions abnormally, the heart may contract in a rate that is abnormally slow or abnormally fast, or that contractions at one or more cardiac regions become chaotic and asynchronized. Such conditions are known as cardiac arrhythmias. Cardiac arrhythmias result in diminished blood flow in the circulatory system and hence insufficient oxygen supply to meet the body's metabolic needs.

Arrhythmias are treated by therapies including, but not being limited to, various types of pacing, cardioversion, and defibrillation therapies delivered by implantable CRM devices. To deliver the right type of therapy with adequate timing, one or more biopotential signals, called electrograms, are sensed to indicate of a cardiac rhythm, including the type of arrhythmia when the cardiac rhythm becomes abnormal. An intracardiac electrogram is sensed with at least one electrode placed in or on the heart. Depending on the location of the electrode, the intracardiac electrogram indicates localized electrical activities of one particular cardiac region. Under certain circumstances, the localized electrical activities may indicate an ongoing arrhythmia but not the origin of that arrhythmia. Additionally, reliability of intracardiac electrogram-based arrhythmia detection may be compromised by noise or poor electrical connections between the heart and the sensing circuit, which occur due to bodily movements and environmental factors.

To enhance the effectiveness of therapy for cardiac arrhythmias, there is a need for enhancement of intracardiac electrogram-based arrhythmia detections.

SUMMARY

A CRM system enhances intracardiac electrogram-based arrhythmia detection using a wireless ECG, which is a signal sensed with implantable electrodes and approximating a surface ECG. In one embodiment, the wireless ECG is a subcutaneous ECG sensed through electrodes implanted in subcutaneous tissue, such as through electrodes incorporated onto an implantable medical device that is subcutaneously implanted.

In one embodiment, a CRM system includes an implantable medical device and a plurality of implantable subcutaneous electrodes. The implantable medical device includes a primary sensing circuit, an auxiliary sensing circuit, a processing circuit, a switch circuit, and a selection circuit. The primary sensing circuit includes an electrogram sensing circuit to sense an intracardiac electrogram. The auxiliary sensing circuit includes a wireless ECG sensing circuit to sense a subcutaneous ECG through the implantable subcutaneous electrodes. The processing circuit receives a signal being one of the intracardiac electrogram and the subcutaneous ECG.

The switch circuit receives a selection signal from the selection circuit and connects one of the primary sensing circuit and the auxiliary sensing circuit to the processing circuit according to the selection signal.

In one embodiment, a method for cardiac signal sensing is provided. An intracardiac electrogram is sensed through an implantable lead. A failure signal indicating a failure in sensing the intracardiac electrogram is detected. A subcutaneous ECG is sensed as a substitute for the intracardiac electrogram if the failure signal is detected.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in the present document.

DETAILED DESCRIPTION

Figure 1:
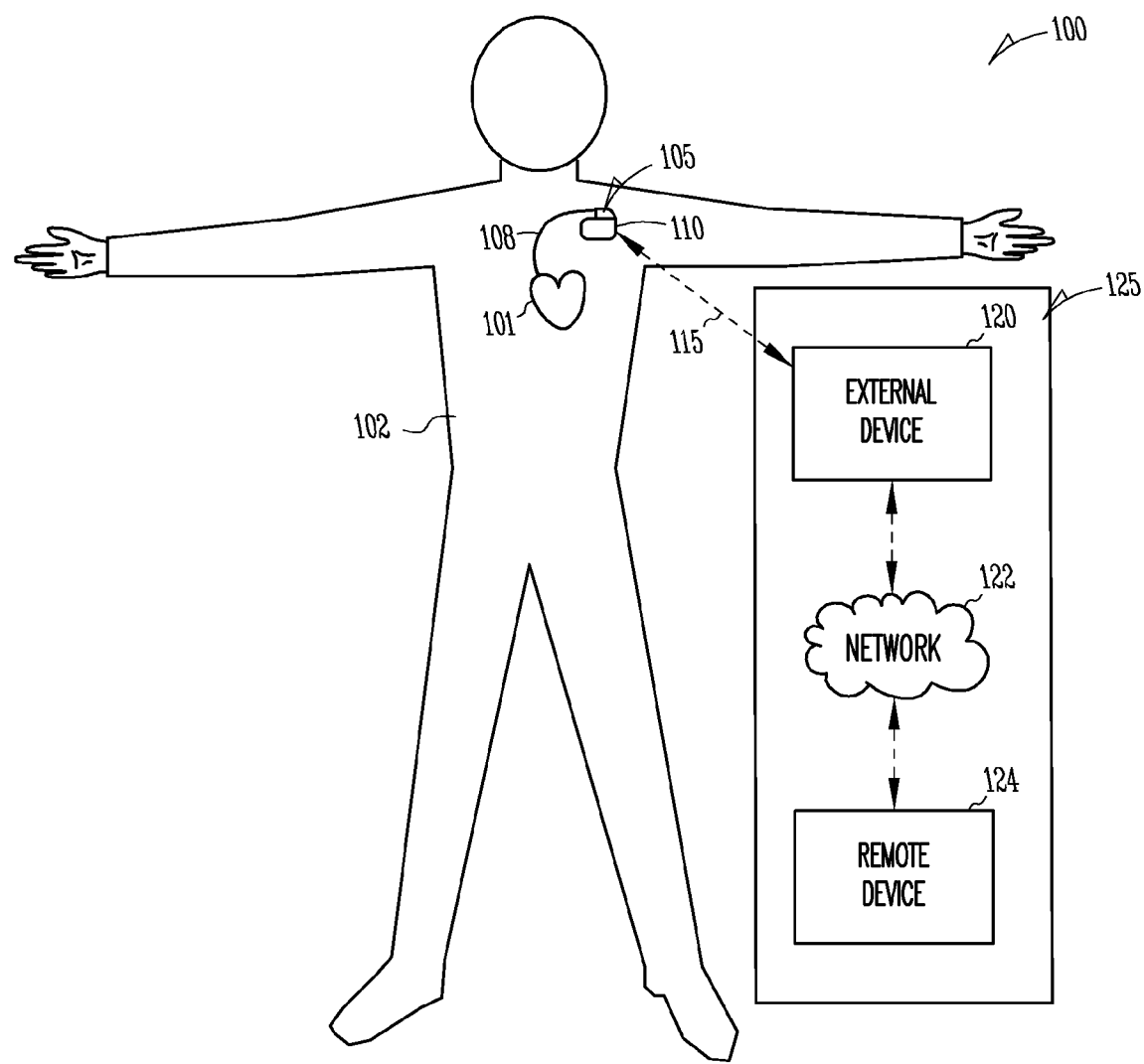
FIG. 1 is an illustration of an embodiment of a CRM system, including an implantable system and an external system, and portions of an environment in which the CRM system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

This document discusses a CRM system that uses a wireless ECG as one of the signals controlling delivery of electrical therapy to a heart. The wireless ECG includes a signal approximating the surface ECG sensed by an implantable medical device without using an electrode attached to the skin. In this document, a "user" includes a physician or other caregiver using the CRM system to treat a patient. "Electrogram" or "intracardiac electrogram" refers to a cardiac electrical signal sensed with one or more sensing electrodes placed in or on the heart. "Surface ECG" refers to a cardiac electrical signal sensed with electrodes attached onto the exterior surface of the skin. "Wireless ECG" refers to a signal approximating the surface ECG, acquired without using surface (non-implantable, skin contact) electrodes. "Subcutaneous ECG" is a form of wireless ECG and includes a cardiac electrical signal sensed through electrodes implanted in subcutaneous tissue, such as through electrodes incorporated onto an implantable medical device that is subcutaneously implanted.

A surface ECG is morphologically different from the intracardiac electrogram because of the difference in the sources that produce these signals. As reflected in their corresponding morphologies, the surface ECG results from electrical activities of the entire heart, while the intracardiac electrogram primarily results from the spread of electrical activity in a region in close proximity to the one or more sensing electrodes placed in or on the heart. The wireless ECG, including but not being limited to the subcutaneous ECG, has a morphology that approximates that of the surface ECG and reflects electrical activities of a substantial portion of the heart, up to the entire heart.

In various embodiments discussed below, the wireless ECG is used for arrhythmia detection and/or classification. An accurate classification of a detected arrhythmia ensures that an adequate therapy is delivered when necessary. When a detected arrhythmia is known or likely to be one of two types of arrhythmias, the arrhythmia classification may include discrimination between the two types of arrhythmias. For example, a tachycardia detected based on a rapid ventricular rate may be one of ventricular tachycardia (VT) and supraventricular tachycardia (SVT). A VT therapy such as a ventricular defibrillation shock should be delivered only if the tachycardia is VT. A classification of this detected tachycardia includes discrimination of VT from SVT. A proper classification of SVT prevents the defibrillation shock from being delivered to a ventricle, thus avoiding unnecessary discomfort to the patient and shortening of the life expectancy of a battery-powered implantable therapeutic device.

According to the present subject matter, a classification and/or confirmation process following an initial detection provides enhancement of arrhythmia detection. In various embodiments, VT detection is enhanced by discriminating VT from SVT following a detection of a rapid ventricular rate and/or by confirming a detection of a VT episode with a separate detection of the same VT episode. In further embodiments, an arrhythmia classification (including discrimination) process is confirmed with a separate classification process applied to the same detected arrhythmia. Thus, in various embodiments, a detection process for a particular type arrhythmia includes an initial detection followed by a classification and/or confirmation process.

FIG. 1 is an illustration of an embodiment of portions of a CRM system 100 and portions of the environment in which system 100 is used. CRM system 100 includes an implantable system 105, an external system 125, and a telemetry link 115 providing for bidirectional communication between implantable system 105 and external system 125. Implantable system 105 includes an implantable medical device 110 and a lead system 108. Implantable medical device 110 is implanted within a body 102 and coupled to a heart 101 via lead system 108. Examples of implantable medical device 110 include, but are not limited to, pacemakers, pacemaker/defibrillators, cardiac resynchronization therapy (CRT) devices, cardiac remodeling control therapy (RCT) devices, and cardiac monitors. In one embodiment, lead system 108 includes multiple atrial and ventricular leads each including one or more electrodes for pacing and/or cardioversion/defibrillation. In one embodiment, external system 125 includes a programmer. In another embodiment, external system 125 is a patient management system including an external device 120 in proximity of implantable device 110, a remote device 124 in a relatively distant location, and a telecommunication network 122 linking external device 120 and remote device 124. The patient management system allows access to implantable system 105 from a remote location, for purposes such as monitoring patient status and adjusting therapies. In one embodiment, telemetry link 115 is an inductive telemetry link. In an alternative embodiment, telemetry link 115 is a far-field radio-frequency (RF) telemetry link. In one embodiment, telemetry link 115 provides for data transmission from implantable medical device 110 to external system 125. This may include, for example, transmitting real-time physiological data acquired by implantable medical device 110, extracting physiological data acquired by and stored in implantable medical device 110, extracting patient history data such as occurrences of arrhythmias and therapy deliveries recorded in implantable medical device 110, and extracting data indicating an operational status of implantable medical device 110 (e.g., battery status and lead impedance). In a further embodiment, telemetry link 115 provides for data transmission from external system 125 to implantable medical device 110. This may include, for example, programming implantable medical device 110 to acquire physiological data, programming implantable medical device 110 to perform at least one self-diagnostic test (such as for a device operational status), and programming implantable medical device 110 to deliver at least one therapy.

Implantable medical device 110 includes circuitry for sensing at least one intracardiac electrogram and at least one wireless ECG. In various embodiments, implantable medical device 110 analyzes the wireless ECG to supplement or enhance intracardiac electrogram-based arrhythmia detection and classification for effective delivery of electrical therapies to heart 101. In other embodiments, implantable medical device 110 senses the wireless ECG as an alternative to an intracardiac electrogram, such as when the wireless ECG is associated with a better signal quality for the purpose of detecting cardiac electrical events.

Figure 2:
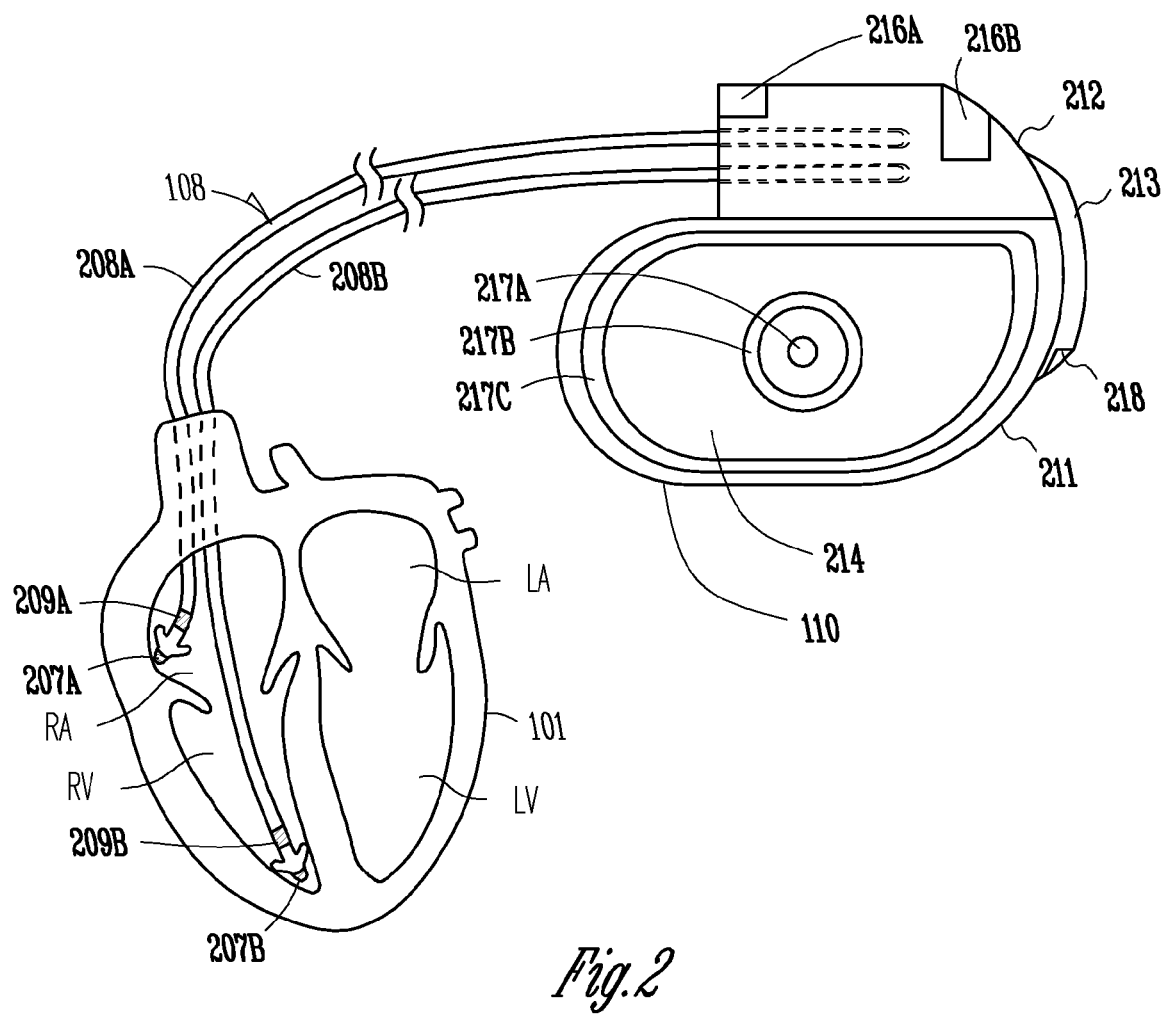
FIG. 2 is an illustration of an exemplary electrode system for wireless ECG sensing.

FIG. 2 is an illustration of one exemplary electrode system for wireless ECG sensing. An electrode system for sensing the wireless ECG includes two or more implantable electrodes. These implantable electrodes are selected from the electrodes including, but not being limited to, those illustrated in FIG. 2. The electrodes are selected to allow for sensing electrical activities from a substantial portion of the heart, up to the entire heart.

In one embodiment, one or more pacing electrodes of lead system 108 are used as one or more electrodes for the wireless ECG sensing. In one embodiment, as illustrated in FIG. 2, lead system 108 includes an atrial lead 208A and a ventricular lead 208B. The one or more electrodes are selected from, for example, a tip electrode 207A of atrial lead 208A, a ring electrode 209A atrial lead 208A, a tip electrode 207B of ventricular lead 208B, and a ring electrode 209B of ventricular lead 208B. Leads 208A-B each have a proximal end connected to implantable medical device 110 and a distal end for intracardiac or epicardial placement. Each tip electrode is located in the distal end of a lead. Each ring electrode is located near the distal end, at a predetermined distance from the tip electrode. In one specific embodiment, atrial lead 208A is an RA lead, and ventricular lead 208B is an RV lead. In another specific embodiment, atrial lead 208A is an RA lead, and ventricular lead 208B is an LV lead. In another specific embodiment, lead system 108 includes only one or more atrial leads. In another specific embodiment, lead system 108 includes only one or more ventricular leads. In other specific embodiments, lead system 108 includes more than one atrial lead or more than one ventricular lead.

Implantable medical device 110 includes a hermetically sealed can 211 to house its circuit. Can 211 has an outer surface subject to contact with body tissue. Can 211 includes or provides for a base of a can electrode 214 that is selectable as one of the electrodes for the wireless ECG sensing. At least a portion of the outer surface of can 211 is made of electrically conductive material. In one embodiment, can 211 is used as can electrode 214. In one specific embodiment, can electrode 214 includes at least one conductive portion of can 211. In another embodiment, can electrode 214 is incorporated onto the outer surface of can 211. Can electrode 214 is electrically insulated from any conductive portion of can 211 using a non-conductive layer. In one specific embodiment, a hermetically sealed feedthrough including a conductor provides for an electrical connection between can electrode 214 and the circuit housed in can 211.

A header 212 is attached to can 211 and includes connectors providing for electrical access to the circuit housed in can 211. In one embodiment, one or more header electrodes 216A-B are incorporated into the header. Header electrodes 216A-B are each selectable as one of the electrodes for the wireless ECG sensing.

In one embodiment, two or more concentric electrodes 217A-C are incorporated onto the outer surface of can 211. Each of the concentric electrodes 217A-C is selectable as one of the electrodes for the wireless ECG sensing. Concentric electrodes 217A-C are insulated from the conductive portion of can 211 with a non-conductive layer and connected to the circuit housed in can 211 via hermetically sealed feedthroughs. In one embodiment, two electrodes, including an inner electrode and an outer electrode, are selected from concentric electrodes 217A-C for the wireless ECG sensing. In one embodiment, the outer electrode has a ring shape. In another embodiment, the outer electrode has a shape approaching the contour of can 211.

In one embodiment, implantable medical device 110 includes an antenna 213 for the far-field RF telemetry. Antenna 213 is electrically connected to the circuit housed in can 211. In one embodiment, antenna 213 projects from header 212 and extends along one side of can 211. In one embodiment, antenna 213 includes a metal conductor with a distal portion exposed for functioning as an antenna electrode 218, which is selectable as one of the electrodes for the wireless ECG sensing.

It is to be understood that the electrodes illustrated in FIG. 2 are intended to be examples but not limitations. Other electrode configurations are usable as long as they provide for sensing of signals that approximates the surface ECG or otherwise contains valuable information for diagnostic and/or therapeutic purposes. In one embodiment, the electrodes for the wireless ECG sensing are selected from the electrodes in one or more leads of lead system 108 (e.g., electrodes 207A, 209A, 207B, and 209B). In this embodiment, it is to be understood that the wireless ECG sensing differs from the electrogram sensing in that their corresponding morphologies reflect the differences in the source of the wireless ECG and the intracardiac electrogram. The electrodes for the wireless ECG sensing are selected to allow for sensing electrical activities from a substantial portion of the heart. This generally means that each pair of electrodes for sensing one wireless ECG includes only one electrode from each lead of lead system 108. In one specific embodiment, electrodes 209A and 209B are selected for the wireless ECG sensing. In another embodiment, the electrodes for the wireless ECG sensing are implantable subcutaneous electrodes. Examples of such implantable subcutaneous electrodes include, but are not limited to electrodes incorporated onto implantable medical device 110, such as can electrode 214, header electrodes 216A-B, concentric electrodes 217A-C, and antenna electrode 218. In this embodiment, the wireless ECG is referred to as subcutaneous ECG, which results from electrical activities of a substantial portion of the heart, up to the entire heart. In another embodiment, the electrodes for the wireless ECG sensing are selected from the electrodes in one or more leads of lead system 108 and the electrodes incorporated onto implantable medical device 110.

In various embodiments in which multiple wireless ECG vectors are needed, multiple pairs of electrodes are selected, simultaneously or one at a time, for a multi-channel (multi-vector) wireless ECG sensing. In one specific embodiment, one or more of wireless ECG vectors are sensed to approximate one or more vectors of a standard multi-lead surface ECG recording. In another specific embodiment, multiple wireless ECG vectors are sensed based on needs of specific information for particular diagnostic purposes. Such wireless ECG vectors do not necessarily approximate standard surface ECG vectors. In one specific embodiment, implantable medical device 110 includes header electrodes 216A-B and can electrode 214 for the wireless ECG sensing. Implantable medical device 110 is programmable for sensing ECG vectors between (1) header electrodes 216A and 216B, (2) header electrode 216A and can electrode 214, and/or (3) header electrode 216B and can electrode 214. In another specific embodiment, implantable medical device 110 includes one of header electrodes 216A-B, antenna electrode 218, and can electrode 214 for the wireless ECG sensing. Implantable medical device 110 is programmable for sensing ECG vectors between (1) header electrode 216A or 216B and antenna electrode 218, (2) header electrode 216A or 216B and can electrode 214, and/or (3) antenna electrode 218 and can electrode 214. In another specific embodiment, implantable medical device 110 includes header electrodes 216A-B, antenna electrode 218, and can electrode 40 for the wireless ECG sensing. Implantable medical device 110 is programmable for sensing ECG vectors between (1) header electrodes 216A and 218, (2) header electrode 216A and antenna electrode 218, (3) header electrode 216A and can electrode 214, (4) header electrode 216B and antenna electrode 218, (5) header electrode 216B and can electrode 214, and/or (6) antenna electrode 218 and can electrode 214. Other specific embodiments involving any electrode combinations for the wireless ECG sensing will be employed based on possible diagnostic and other medical needs and considerations.

The selection of ECG vectors depends on the purpose for the wireless ECG sensing. In one embodiment, the wireless ECG is sensed for detecting atrial depolarizations (P waves), and the ECG vector that provide for a reliable P wave detection are selected. In another embodiment, the wireless ECG is sensed for detecting ventricular depolarizations (R waves), and one or more ECG vectors that provide for a reliable R wave detection are selected. In another embodiment, the wireless ECG is sensed for a global view of all cardiac activities, one or more ECG vectors that provide such global view, either alone or in combination, are selected. In one embodiment, when more than one ECG vector provides for a reliable sensing for a particular purpose, the ECG vector showing the highest signal-to-noise ratio (SNR) for that purpose is selected. For example, if the wireless ECG is sensed for detecting P waves, the ECG vector showing the highest SNR with P waves being considered as the signal is selected.

Figure 3:
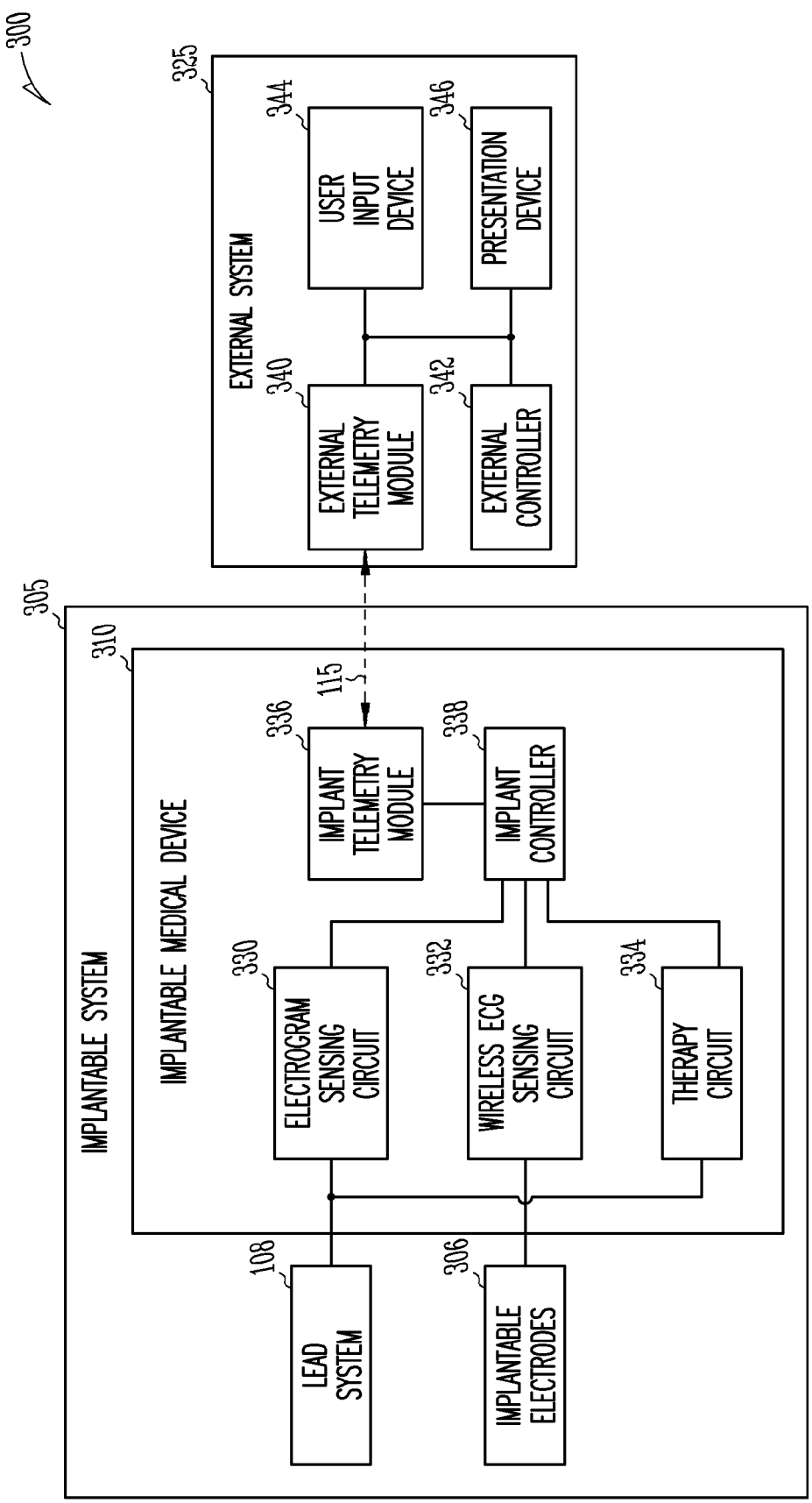
FIG. 3 is a block diagram illustrating an embodiment of portions of a circuit of the CRM system.

FIG. 3 is a block diagram illustrating an embodiment of portions of a circuit of a CRM system 300. CRM system 300 represents one embodiment of CRM system 100 and includes an implantable system 305, which is one embodiment of implantable system 105, and an external system 325, which is one embodiment of external system 125. Telemetry link 115 provides bi-directional communication between implantable system 305 and external system 325.

Implantable system 305 includes lead system 108, implantable electrodes 306, and implantable medical device 310. Implantable electrodes 306 are electrodes for the wireless ECG sensing and include, but are not limited to, any two or more electrodes discussed above with reference to FIG. 2. In various embodiments, specific configurations of implantable electrodes 306 are selected according to specific purposes of the wireless ECG sensing. In one embodiment, implantable electrodes 306 include at least one electrode incorporated onto implantable medical device 310. In a further embodiment, implantable electrodes 306 include two or more electrodes incorporated onto implantable medical device 310 for sensing one or more subcutaneous ECGs. In one embodiment, implantable electrodes 306 include at least one electrode incorporated into a lead of lead system 108. In one embodiment, implantable electrodes 306 include two or more electrodes incorporated into lead system 108 for sensing one or more intracardiac signals each approximating a surface ECG. Implantable medical device 310 is an embodiment of implantable medical device 110 and includes an electrogram sensing circuit 330, a wireless ECG sensing circuit 332, a therapy circuit 334, an implant telemetry module 336, and an implant controller 338. Sensing circuit 330 senses one or more intracardiac electrograms from one or more of RA, RV, LA, and LV. Wireless ECG sensing circuit 332 senses one or more wireless ECGs. An example of a circuit for sensing the wireless ECG is discussed in U.S. patent application Ser. No. 10/795,126, entitled "WIRELESS ECG IN IMPLANTABLE DEVICES," filed on Mar. 5, 2004, assigned to Cardiac Pacemakers, Inc., which is incorporated by reference in its entirety. Therapy circuit 334 delivers a therapy or a signal controlling a therapy. In one embodiment, therapy circuit 334 includes a therapy output circuit delivering an electrical energy to the heart through lead system 108. Example of such a therapy output circuit includes a pacing circuit and a cardioversion/defibrillation circuit. In this embodiment, lead system 108 includes at least one lead with at least one electrode configured for delivering pacing or cardioversion/defibrillation pulses to the heart. In another embodiment, therapy circuit 334 includes a substance delivery circuit to deliver one or more chemical and/or biological agents. In another embodiment, therapy circuit 334 includes a therapy control signal generator to transmit a signal controlling a therapy delivered by another device. Implant telemetry module 336 receives commands or other data from external system 325 and transmits acquired signals and other data to external system 325. Implant controller 338 controls the operation of implantable medical device 310 based commands received from external system 325 and acquired signals including, but not being limited to, the one or more intracardiac electrograms and the one or more wireless ECGs. In one embodiment, other physiological signals are also acquired and used by implantable medical device 310 to control its operation, such as acceleration signals indicative of gross physical activity and/or heart sounds, blood pressure signals, thoracic impedance signals, and other signals indicative of hemodynamic performance or properties of cardiac tissue or blood.

In one embodiment, one or more wireless ECGs are sensed and transmitted to external system 325 for diagnostic purposes. In another embodiment, one or more wireless ECGs sensed and transmitted to external system 325 for therapeutic purposes, such as for decisions to start, stop, or adjust a therapy or for therapy optimization. In another embodiment, one or more wireless ECGs are processed by implant controller 338 to be used as one or more signals controlling therapy delivery by implantable medical device 310. In another embodiment, one or more wireless ECGs are sensed for use by implant controller 338 and transmission to external system 325.

External system 325 includes an external telemetry module 340, an external controller 342, a user input device 344, and a presentation device 346. External telemetry module 340 receives acquired signals or other data from implantable medical device 310 and transmits commands and other data to implantable medical device 310. External controller 342 controls the operation of external system 325. User input device 344 and presentation device 346 are part of a user interface allowing a user to control the operation of CRM system 300. User input device 344 receives commands and other information from the user for programming implantable medical device 310 as well as external system 325. In one embodiment, presentation device 346 presents acquired signals including the one or more intracardiac electrograms and the one or more wireless ECGs. In a further embodiment, the user selects one or more signals from the one or more intracardiac electrograms and the one or more wireless ECGs for particular purposes by programming implantable medical device 310.

Various specific embodiments of implantable system 305 are discussed below with reference to FIGS. 4-16 as examples illustrating applications of the wireless ECG sensing in a CRM system including an implantable device.

EXAMPLE 1

Arrhythmia Detection Enhancement

Figure 4:
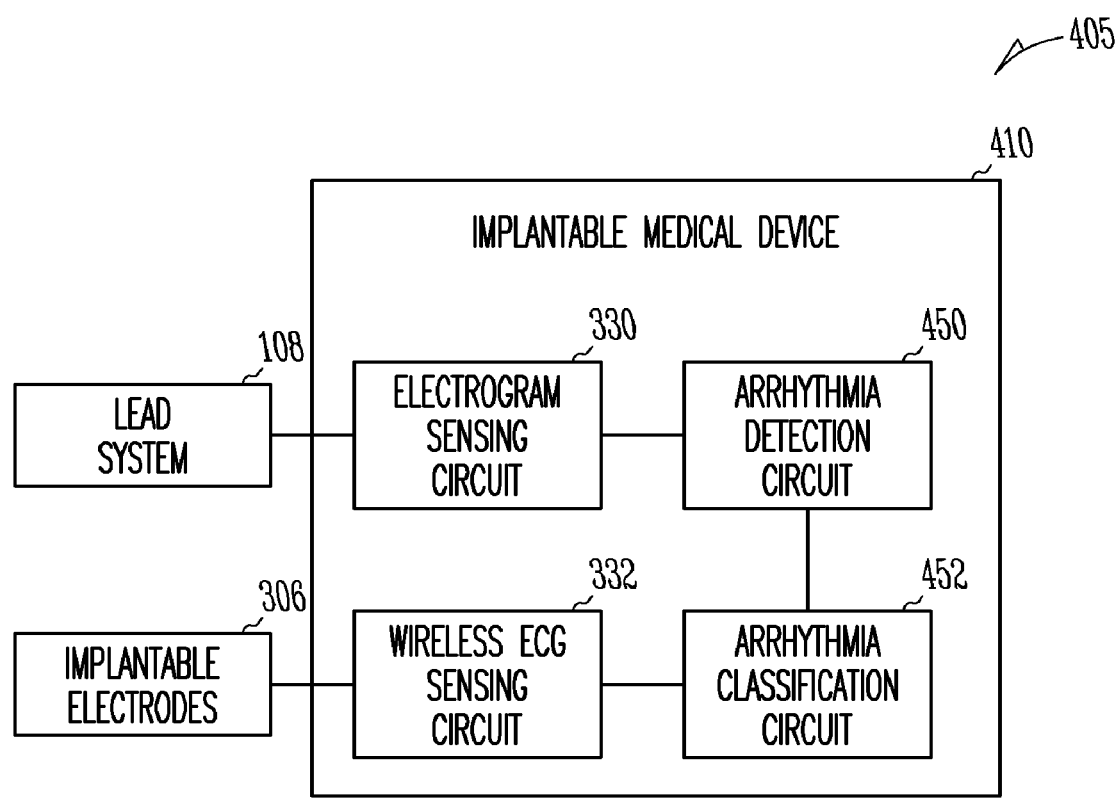
FIG. 4 is a block diagram illustrating an embodiment of portions of an implantable system including a circuit providing for ventricular arrhythmia detection enhancement using the wireless ECG.

FIG. 4 is a block diagram illustrating an embodiment of portions of an implantable system 405 including a circuit providing for ventricular arrhythmia detection enhancement using the wireless ECG. Implantable system 405 includes lead system 108 for intracardiac electrogram sensing, implantable electrodes 306 for wireless ECG sensing, and an implantable medical device 410. In one embodiment, implantable system 405 is part of implantable system 305.

Implantable medical device 410 includes electrogram sensing circuit 330, wireless ECG sensing circuit 332, an arrhythmia detection circuit 450, and an arrhythmia classification circuit 452. Arrhythmia detection circuit 450 detects an arrhythmia based on at least one intracardiac electrogram sensed by electrogram sensing circuit 330 through lead system 108. Arrhythmia classification circuit 452 classifies the detected arrhythmia based on at least one wireless ECG sensed by wireless ECG sensing circuit 332 through implantable electrodes 306. For example, arrhythmia detection circuit 450 detects a tachycardia based on a ventricular rhythm detected from a ventricular electrogram showing ventricular depolarizations (R waves). Arrhythmia classification circuit 452 classifies the detected tachycardia as one of VT and SVT based an atrial rhythm detected from a wireless ECG including detectable atrial depolarizations (P waves).

Figure 5:
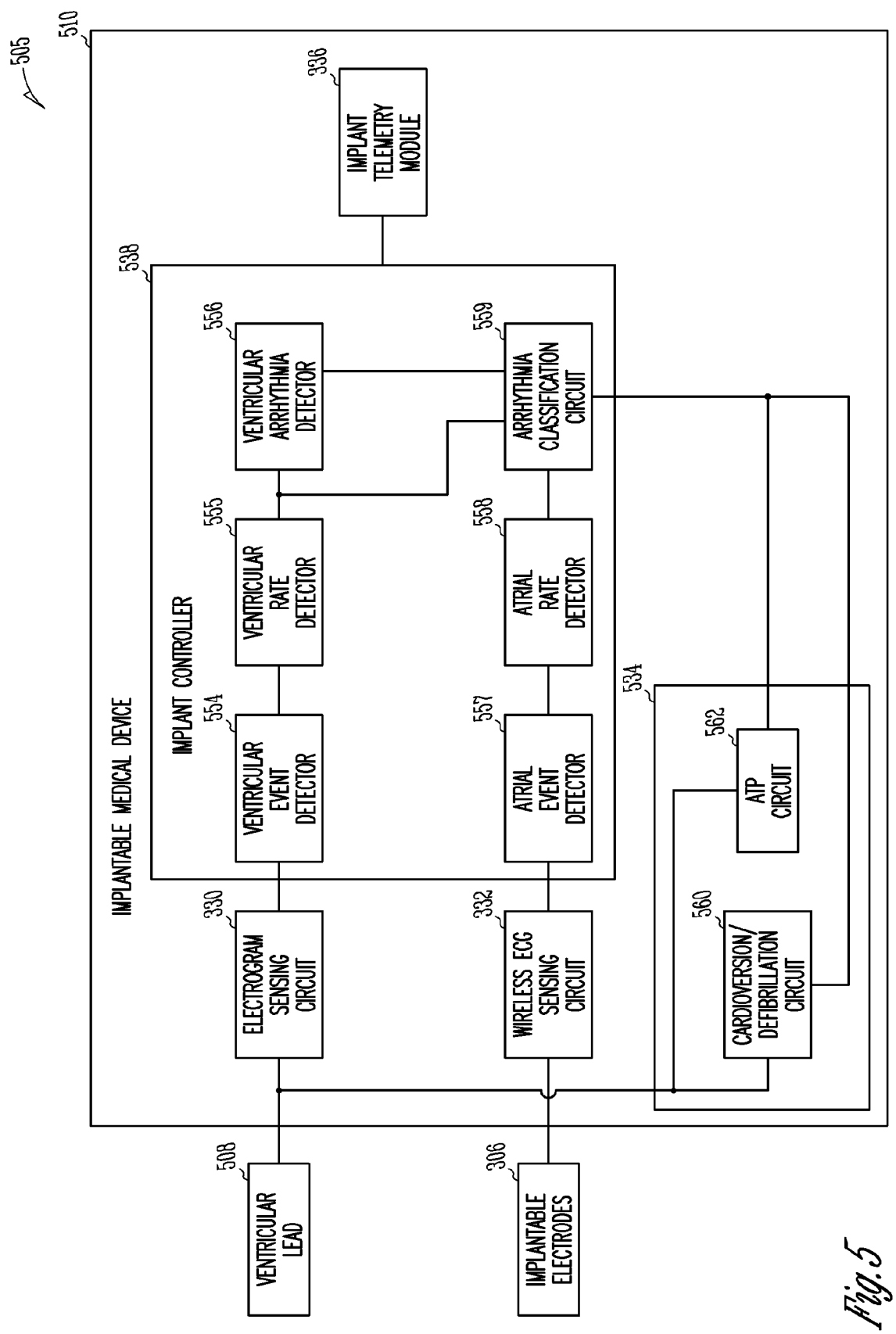
FIG. 5 is a block diagram illustrating an embodiment of portions of another implantable system including the circuit providing for ventricular arrhythmia detection enhancement using the wireless ECG.

FIG. 5 is a block diagram illustrating an embodiment of portions of an implantable system 505 including the circuit providing for ventricular arrhythmia detection enhancement using the wireless ECG. Implantable system 505 is a specific embodiment of implantable system 305 and incorporates the general concept, structure, and functions of implantable system 405 as discussed above. Implantable system 505 includes ventricular lead 508 for sensing a ventricular electrogram and delivering electrical energy to a ventricle, implantable electrodes 306 for sensing a wireless ECG indicative of atrial depolarizations, and an implantable medical device 510. Ventricular lead 508 is a defibrillation lead being a lead of lead system 108. Implantable medical device 510 is a specific embodiment of implantable medical device 310 and includes electrogram sensing circuit 330, wireless ECG sensing circuit 332, therapy circuit 534, implant controller 538, and implant telemetry module 336. In one embodiment, implantable medical device 510 is a ventricular defibrillator including two or more electrodes for sensing the wireless ECG. The wireless ECG provides monitoring of atrial activities without the need of placing a sensing electrode in the atria. In one embodiment, implantable electrodes 306 are incorporated onto implantable medical device 510 for sensing a subcutaneous ECG as the wireless ECG.

In one embodiment, therapy circuit 534 includes a cardioversion/defibrillation circuit 560 to deliver ventricular cardioversion/defibrillation pulses to the heart through ventricular lead 508. In a further embodiment, therapy circuit 534 also includes an anti-tachycardia pacing (ATP) circuit 562 to deliver ATP pulses to the heart through ventricular lead 508.

Implant controller 538 includes a ventricular event detector 554, a ventricular rate detector 555, a ventricular arrhythmia detector 556, an atrial event detector 557, an atrial rate detector 558, and an arrhythmia classification circuit 559. Ventricular event detector 554 detects ventricular events including ventricular depolarizations (R waves) from the ventricular electrogram sensed by electrogram sensing circuit 330 through ventricular lead 508. Ventricular rate detector 555 detects a ventricular rate being the number of ventricular events detected over a minute (beats per minute). Ventricular arrhythmia detector 556 detects a ventricular arrhythmia when the ventricular rate exceeds a predetermined tachycardia threshold rate. In one embodiment, ventricular arrhythmia detector 556 detects two or more types of ventricular arrhythmias based on the ventricular rate and predetermined threshold rates each associated with one type of ventricular arrhythmia. In one specific embodiment, ventricular arrhythmia detector 556 includes at least a VT detector that detects VT based on a predetermined threshold VT rate and a ventricular fibrillation (VF) detector that detects VF based on a predetermined threshold VF rate. Atrial event detector 557 detects atrial events including atrial depolarizations (P waves) from the wireless ECG sensed by wireless ECG sensing circuit 332 through implantable electrodes 306. Atrial rate detector 558 detects the atrial rate being the number of atrial events detected over a minute (beats per minute). When a ventricular arrhythmia is detected by ventricular arrhythmia detector 538, arrhythmia classification circuit 559 classifies the detected arrhythmia by discriminating between a ventricular arrhythmia of a ventricular origin and a ventricular arrhythmia of a supraventricular origin. Arrhythmia classification circuit 559 includes a rate comparator to compare the atrial rate and the ventricular rate. The rate comparator includes an input to receive the atrial rate, another input to receive the ventricular rate, and an output indicative of an arrhythmia type classified based on the comparison between the atrial and ventricular rate. In one embodiment, ventricular arrhythmia detector 556 detects VT or VF. If the ventricular rate is substantially greater than the atrial rate, arrhythmia classification circuit 559 classifies the detected VT or VF as a tachycardia or fibrillation of a ventricular origin. A detection of VF or VT is declared or indicated only after an arrhythmia is detected by ventricular arrhythmia detector 538 and classified as VT or VF by arrhythmia classification circuit 559. The classification enhances the detection of VT or VF by confirming that a detected arrhythmia is indeed of ventricular origin before applying a ventricular cardioversion/defibrillation or ventricular ATP therapy. In one embodiment, cardioversion/defibrillation circuit 560 delivers a cardioversion/defibrillation therapy after a detected tachycardia or fibrillation is classified as a tachycardia or fibrillation of ventricular origin. In one embodiment, in addition to the classification of the VT or VF based on the comparison between the ventricular rate and atrial rate, implant controller 538 includes other detection enhancement features known as therapy inhibitors. Such therapy inhibitors prevent the delivery of a cardioversion/defibrillation therapy when certain events or conditions are detected while ventricular arrhythmia detector 556 detects VT or VF. Examples of such therapy inhibitors are discussed in U.S. Pat. No. 6,493,579, "SYSTEM AND METHOD FOR DETECTION ENHANCEMENT PROGRAMMING," assigned to Cardiac Pacemakers, Inc., which is hereby incorporated by reference in its entirety. In one embodiment, implant controller 538 is programmed to cause cardioversion/defibrillation circuit 560 to deliver a cardioversion/defibrillation therapy immediately after arrhythmia classification circuit 559 determines that the ventricular rate is substantially greater than the atrial rate, regardless of the status of other therapy inhibitors. In other words, the detection enhancement based on the comparison between the ventricular rate and atrial rate is programmable for bypassing all other detection enhancement features in implant controller 538 in determining the delivery of the cardioversion/defibrillation therapy. Ventricular lead 508 includes at least one cardioversion/defibrillation electrode. In a further embodiment, ATP circuit 562 delivers ventricular ATP pulses after a detected tachycardia is classified as a tachycardia of ventricular origin. Ventricular lead 508 further includes at least one pacing electrode.

Figure 6:
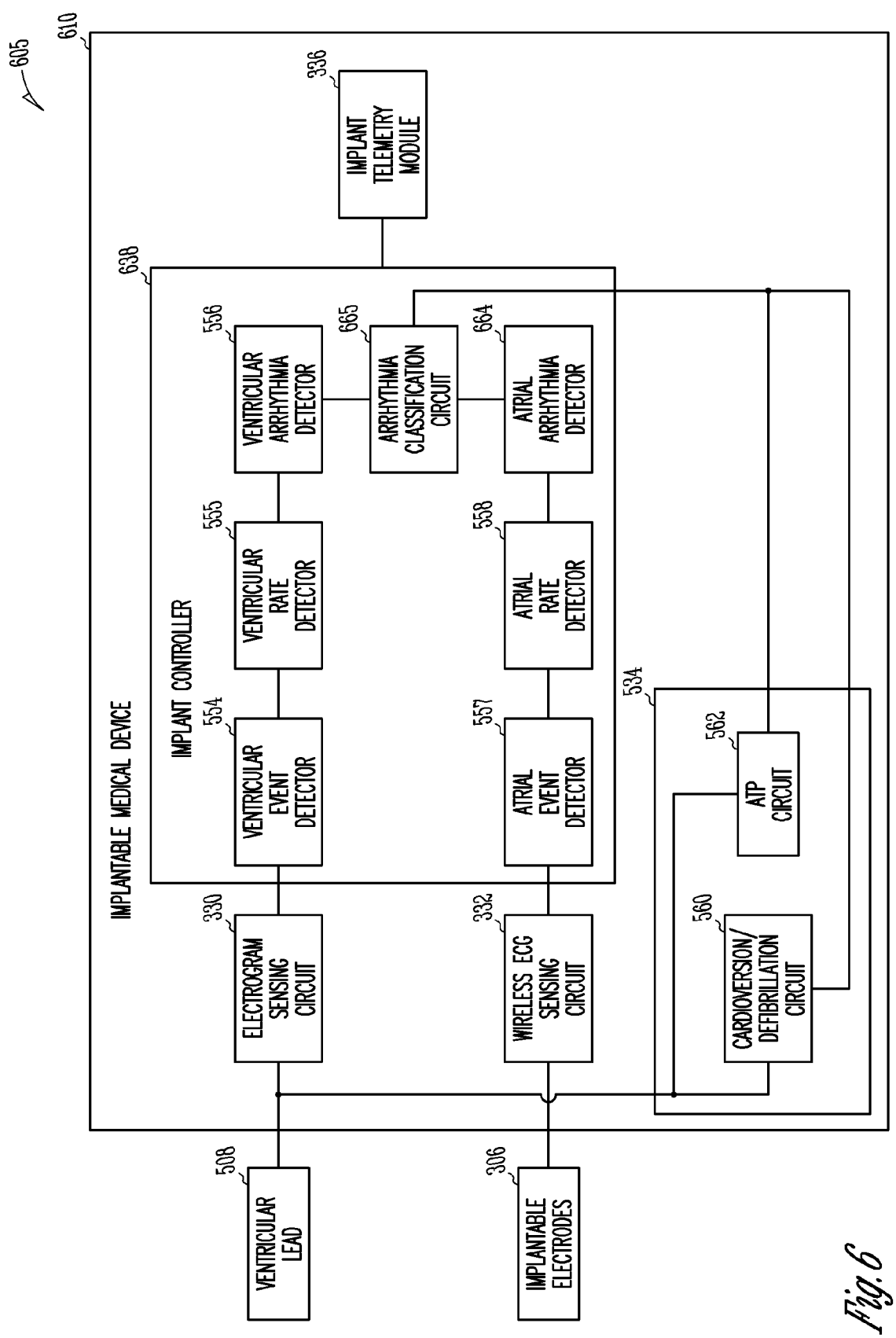
FIG. 6 is a block diagram illustrating an embodiment of portions of another implantable system including the circuit providing for ventricular arrhythmia detection enhancement using the wireless ECG.

FIG. 6 is a block diagram illustrating an embodiment of portions of an implantable system 605 including the circuit providing for ventricular arrhythmia detection enhancement using the wireless ECG. Implantable system 605 is a specific embodiment of implantable system 305 and incorporates the general concept, structure, and functions of implantable system 405 as discussed above. Implantable system 605 includes ventricular lead 508, implantable electrodes 306, and an implantable medical device 610. Implantable medical device 610 is a specific embodiment of implantable medical device 310 and includes electrogram sensing circuit 330, wireless ECG sensing circuit 332, therapy circuit 534, implant controller 638, and implant telemetry module 336. In one embodiment, implantable medical device 510 is a ventricular defibrillator including two or more electrodes for sensing the wireless ECG. The wireless ECG provides monitoring of atrial activities without the need of placing a sensing electrode in the atria. In one embodiment, implantable electrodes 306 are incorporated onto implantable medical device 610 for sensing a subcutaneous ECG as the wireless ECG. Implantable medical device 610 differs from implantable medical device 510 by using another approach to the classification of the detected VT.

Implant controller 638 includes ventricular event detector 554, ventricular rate detector 555, ventricular arrhythmia detector 556, atrial event detector 557, atrial rate detector 558, an atrial arrhythmia detector 664, and an arrhythmia classification circuit 665. Atrial arrhythmia detector 664 detects an atrial arrhythmia when the atrial rate exceeds a predetermined tachycardia threshold rate. In one embodiment, atrial arrhythmia detector 664 includes an atrial fibrillation (AF) detector to detect AF and an atrial tachycardia (AT) detector to detect AT such as atrial flutter. Arrhythmia classification circuit 665 includes a specificity enhancement circuit to classify the detected ventricular arrhythmia by discriminating between a ventricular arrhythmia of a ventricular origin and a ventricular arrhythmia of a supraventricular origin. The discrimination is at least partially based on whether an atrial arrhythmia is concurrently detected. If atrial arrhythmia is not concurrently detected, the detected ventricular arrhythmia is classified as an arrhythmia of a ventricular origin. If atrial arrhythmia is concurrently detected, further detection and/or classification is required to determine whether the detected ventricular arrhythmia has a supraventricular origin or both supraventricular and ventricular origins. In one embodiment, ventricular arrhythmia detector 556 detects VT or VF. If no atrial arrhythmia including AF and atrial flutter is detected, the specificity enhancement circuit of arrhythmia classification circuit 559 classifies the detected tachycardia or fibrillation as a tachycardia or fibrillation of a ventricular origin. If an atrial arrhythmia such as an AF or atrial flutter is detected, the specificity enhancement circuit of arrhythmia classification circuit 559 performs additional analysis, such as morphology-based analysis of the ventricular electrogram, to determine whether to classify the detected tachycardia or fibrillation as a tachycardia or fibrillation of a supraventricular origin or a ventricular origin.

Figure 7:
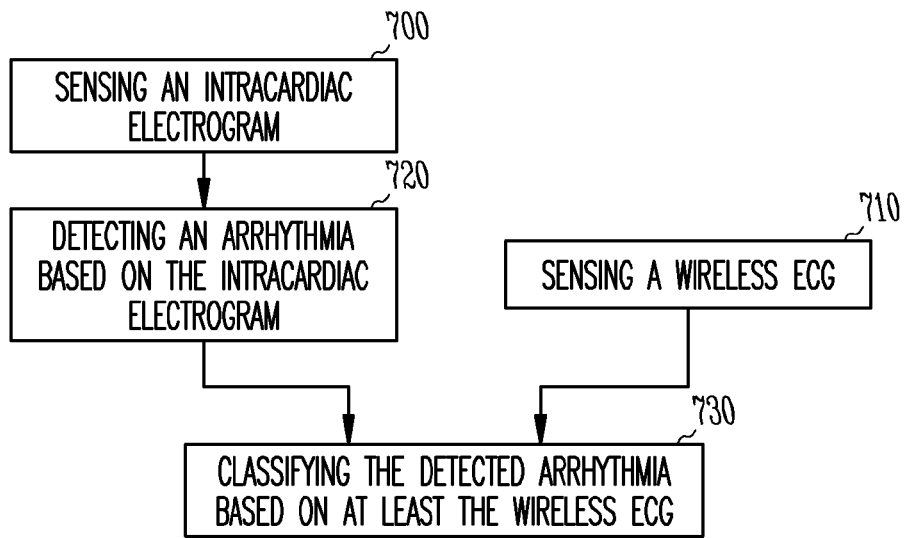
FIG. 7 is a flow chart illustrating an embodiment of a method for ventricular arrhythmia detection enhancement using the wireless ECG.

FIG. 7 is a flow chart illustrating an embodiment of a method for ventricular arrhythmia detection enhancement using the wireless ECG. In one embodiment, the method is performed by a CRM system such as implantable system 405, implantable system 505, or implantable system 605.

An intracardiac electrogram is sensed at 700. Concurrently, a wireless ECG is sensed at 710. Arrhythmia is detected based on the intracardiac electrogram at 720. The detected arrhythmia is classified based on at least the wireless ECG at 730. In one embodiment, the classification includes discrimination between an arrhythmia of ventricular origin and an arrhythmia of atrial origin.

In one embodiment, a ventricular electrogram is sensed at 700. Ventricular events are detected from the ventricular electrogram. A ventricular rate is detected as the number of ventricular events detected over a minute. At least one of a tachycardia and fibrillation is detected based on the ventricular electrogram at 720. To classify the detected tachycardia or fibrillation, atrial events are detected from the wireless ECG. An atrial rate is detected as the number of atrial events detected over a minute. The detected tachycardia or fibrillation is classified as a tachycardia or fibrillation of ventricular origin if the ventricular rate is substantially greater than the atrial rate. In one embodiment, the detected tachycardia or fibrillation is classified as a tachycardia or fibrillation of ventricular origin if the ventricular rate is greater than the atrial rate by at least a predetermined rate margin. In one specific embodiment, the rate margin is programmed to about 10 beats per minute.

In another embodiment, a ventricular electrogram is sensed at 700. Ventricular events are detected from the ventricular electrogram. A ventricular rate is detected as the number of ventricular events detected over a minute. At least one of a tachycardia and fibrillation is detected based on the ventricular electrogram at 720. To classify the detected tachycardia or fibrillation, atrial arrhythmia is detected from the wireless ECG. This includes detection of at least one of AF and atrial flutter. If the atrial arrhythmia is not detected, the detected tachycardia or fibrillation is classified as VT or VF. If the atrial arrhythmia is detected, further analysis, such as morphological analysis of the ventricular electrogram, is performed to determine whether to classify the detected tachycardia or fibrillation as tachycardia or fibrillation having a ventricular origin or both supraventricular and ventricular origins.

In one embodiment, a ventricular cardioversion/defibrillation shock is delivered to the heart after a detected tachycardia or fibrillation is classified as a tachycardia or fibrillation of ventricular origin. In a further embodiment, ventricular ATP pulses are delivered to the heart after a detected tachycardia is classified as a tachycardia of ventricular origin. In one embodiment, ventricular arrhythmia detection is enhanced by the rate comparison and one or more additional methods that detect events and conditions indicative or suggestive of a need to inhibit the ventricular cardioversion/defibrillation shock. If the detected tachycardia or fibrillation is classified as a tachycardia or fibrillation of ventricular origin based on that the ventricular rate is substantially greater than the atrial rate, the ventricular cardioversion/defibrillation shock is delivered immediately, regardless of any result produced by the one or more addition methods.

EXAMPLE 2

Backup Sensing in Lead Failure Mode

Figure 8:
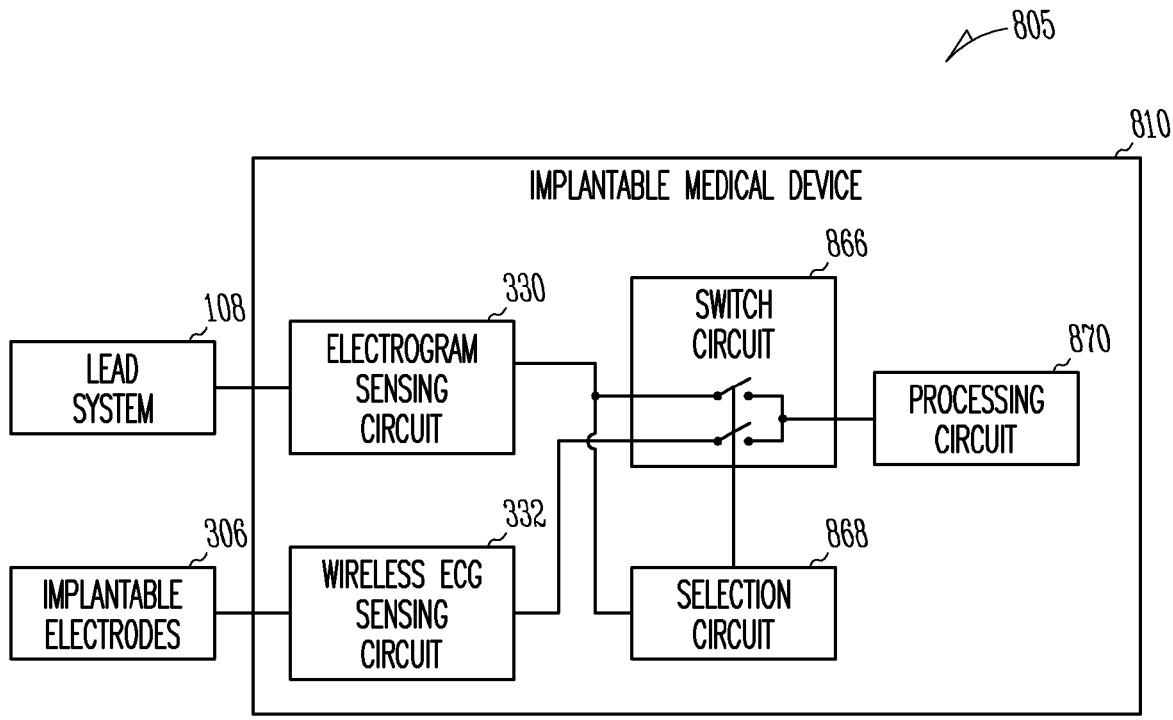
FIG. 8 is a block diagram illustrating an embodiment of portions of an implantable system including a circuit using the wireless ECG for backup sensing.

FIG. 8 is a block diagram illustrating an embodiment of portions of an implantable system 805 including a circuit using the wireless ECG for backup sensing. The backup sensing is needed when a normal or primary sensing circuit no longer provides for reliable sensing of cardiac activities. Implantable system 805 includes lead system 108 for electrogram sensing, implantable electrodes 306 for wireless ECG sensing, and an implantable medical device 810. In one embodiment, implantable system 805 is part of implantable system 305.

Implantable medical device 810 includes electrogram sensing circuit 330, wireless ECG sensing circuit 332, a switch circuit 866, a selection circuit 868, and a processing circuit 870. Electrogram sensing circuit 330 is used as a primary sensing circuit for implantable medical device 810 and senses an intracardiac electrogram. Wireless ECG sensing circuit 332 is used as an auxiliary sensing circuit for implantable medical device 810 and senses a wireless ECG. Processing circuit 870 includes an input to receive a cardiac signal selected from one of the intracardiac electrogram and the wireless ECG. Switch circuit 866 connects the input of processing circuit 870 and one of electrogram sensing circuit 330 and wireless ECG sensing circuit 332 according to a selection signal. The selection signal determines which of the intracardiac electrogram and the wireless ECG is routed to processing circuit 870 for further processing. Selection circuit 868 produces the selection signal in response to an indication of a failure mode in which the primary sensing circuit fails to provide reliable sensing. The failure mode results from, for example, a dislodgment or breakage of the lead connected to electrogram sensing circuit 330 for the electrogram sensing. The wireless ECG provides for backup sensing as part of a failure mode operation until implantable medical device 810 exits the failure mode, for example, when the lead problem is corrected. In one embodiment, selection circuit 868 also produces the selection signal in response to a command transmitted from external system 325. The command represents a user's selection of a cardiac signal.

Figure 9:
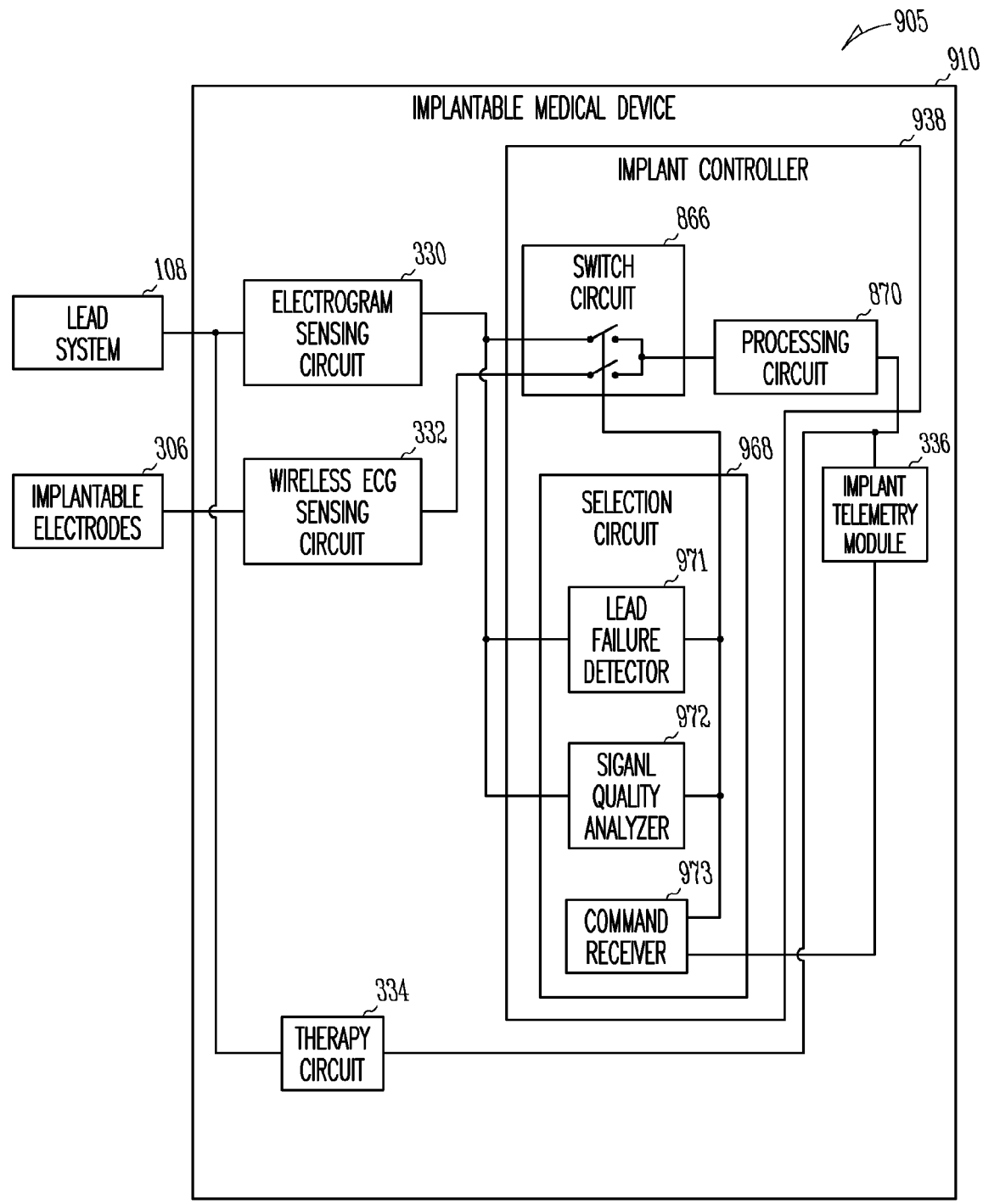
FIG. 9 is a block diagram illustrating an embodiment of portions of another implantable system including the circuit using the wireless ECG for backup sensing.

FIG. 9 is a block diagram illustrating an embodiment of portions of an implantable system 905 including the circuit using the wireless ECG for backup sensing. Implantable system 905 is a specific embodiment of implantable system 305 and incorporates the general concept, structure, and functions of implantable system 805 as discussed above. Implantable system 905 includes lead system 108, implantable electrodes 306, and an implantable medical device 910. Implantable medical device 910 is a specific embodiment of implantable medical device 310 and includes electrogram sensing circuit 330, wireless ECG sensing circuit 332, therapy circuit 334, implant controller 938, and implant telemetry module 336. In one embodiment, implantable electrodes 306 are incorporated onto implantable medical device 910 for sensing a subcutaneous ECG as the wireless ECG.

Implant controller 938 includes switch circuit 866, selection circuit 968, and processing circuit 870. Selection circuit 968 is a specific embodiment of selection circuit 868. In one embodiment, selection circuit 968 includes a lead failure detector 971, a signal quality analyzer 972, and a command receiver 973. In another embodiment, selection circuit 968 includes any one or two of lead failure detector 971, signal quality analyzer 972, and command receiver 973. Lead failure detector 971 detects a lead failure that substantially affects the quality of the intracardiac electrogram. Selection circuit 968 produces the selection signal to connect the input of processor 870 to wireless ECG sensing circuit 332 when the lead failure is detected. In one embodiment, lead failure detector 971 includes a lead impedance measurement circuit to measure a lead impedance as applied to electrogram sensing circuit 330. Selection circuit 968 produces the selection signal to connect the input of processor 870 to wireless ECG sensing circuit 332 when the lead impedance exceeds a predetermined threshold impedance value. Signal quality analyzer 972 analyzes a measure of quality of the intracardiac electrogram and produces a quality parameter indicative of the quality of the intracardiac electrogram. Selection circuit 968 produces the selection signal to connect the input of processor 870 to wireless ECG sensing circuit 332 when the quality parameter is below a predetermined threshold parameter value. In one embodiment, signal quality analyzer 972 includes an SNR measurement circuit to measure the SNR of the intracardiac electrogram. Selection circuit 968 produces the selection signal to connect the input of processor 870 to wireless ECG sensing circuit 332 when the SNR is below a predetermined threshold ratio. Command receiver 973 receives an external command entered by the user through user input 344 of external system 325. Selection circuit 968 produces the selection signal to connect the input of processor 870 to one of or electrogram sensing circuit 320 and wireless ECG sensing circuit 332 based on the external command. In one embodiment, the user decides to use the wireless ECG for backup sensing in response to a lead problem or poor electrogram quality presented through presentation device 346. The wireless ECG serves as a substitute signal for the intracardiac electrogram until reliable intracardiac electrogram sensing by electrogram sensing circuit 330 is resumed, such as when the lead for the intracardiac electrogram sensing is reconnected, repositioned, or replaced.

Figure 10:
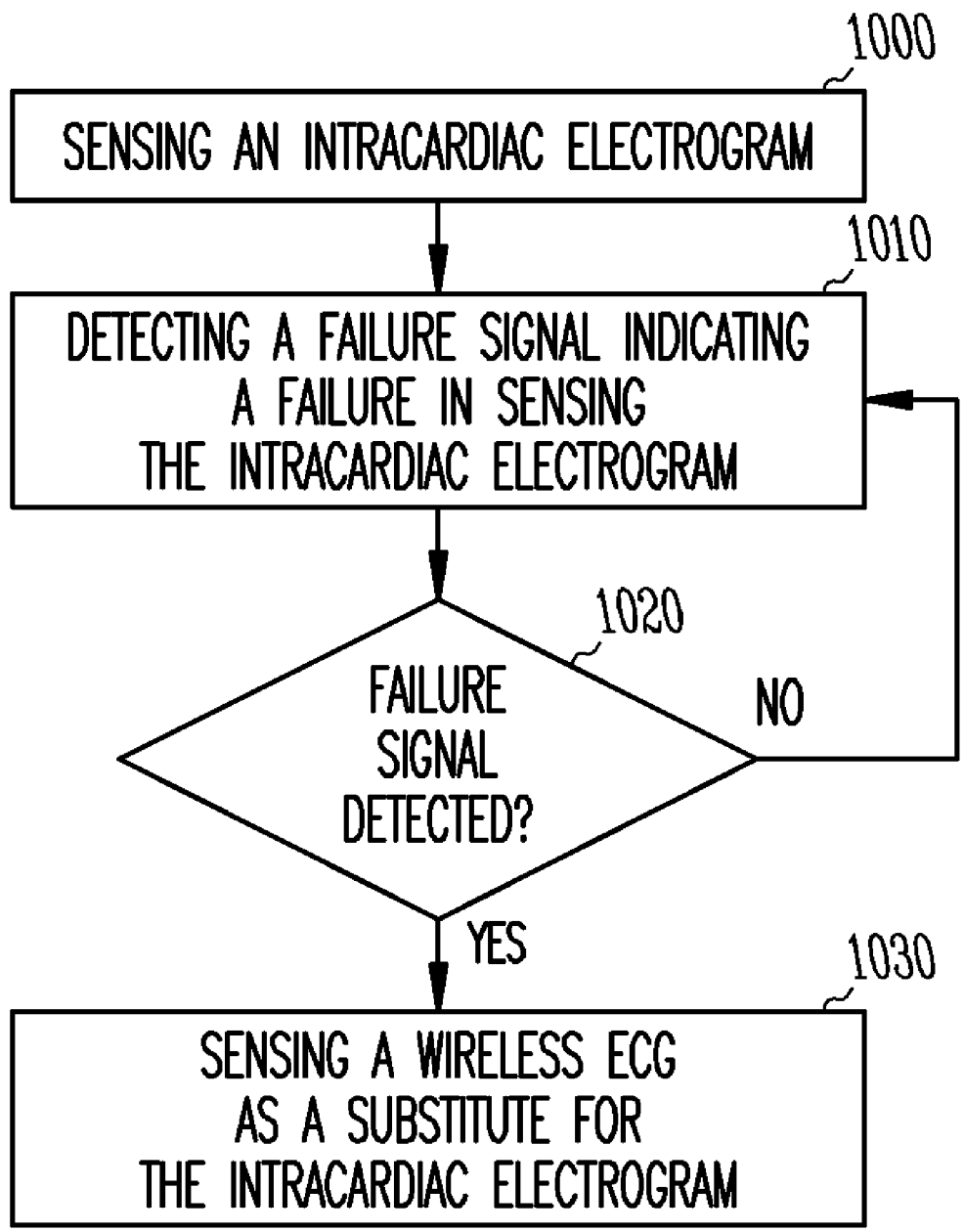
FIG. 10 is a flow chart illustrating an embodiment of a method for using the wireless ECG for backup sensing.

FIG. 10 is a flow chart illustrating an embodiment of a method for using the wireless ECG for backup sensing. In one embodiment, the method is performed by a CRM system including implantable system 805 or implantable system 905.

An intracardiac electrogram is sensed through an implantable lead with at least one intracardiac electrode at 1000. A failure signal indicating a failure in sensing the intracardiac electrogram is detected at 1010. If the failure signal is detected at 1020, a wireless ECG is sensed as a substitute for the intracardiac electrogram at 1030.

In one embodiment, the failure signal is a signal indicative of a lead failure that substantially affects the quality of the intracardiac electrogram. In one specific embodiment, the failure signal includes a signal indicative of lead impedance. The lead impedance indicates a dislodgement or breakage of an implantable lead used for sensing the intracardiac electrogram.

In another embodiment, the failure signal is a signal indicative of poor electrogram quality. A quality parameter indicative of a quality of the intracardiac electrogram is produced based on an analysis of the intracardiac electrogram. The failure signal is produced when the quality parameter falls below a predetermined threshold parameter value. In one specific embodiment, the quality of the intracardiac electrogram is indicated by the SNR of the intracardiac electrogram. The failure signal is produced when the SNR is below a predetermined threshold ratio.

In another embodiment, the failure signal is an external command entered by the user. The user enters the command for using the wireless ECG as a substitute for the intracardiac electrogram when informed of a problem affecting the reliably of intracardiac electrogram sensing or upon observation of such a problem.

In one embodiment, the failure signal includes any one or more of the signal indicative of the lead failure, the signal indicative of poor electrogram quality, and the external command. The wireless ECG is used as the substitute for the intracardiac electrogram when at least one of those failure signals is detected.

EXAMPLE 3

Alternative Sensing Vector

Figure 11:
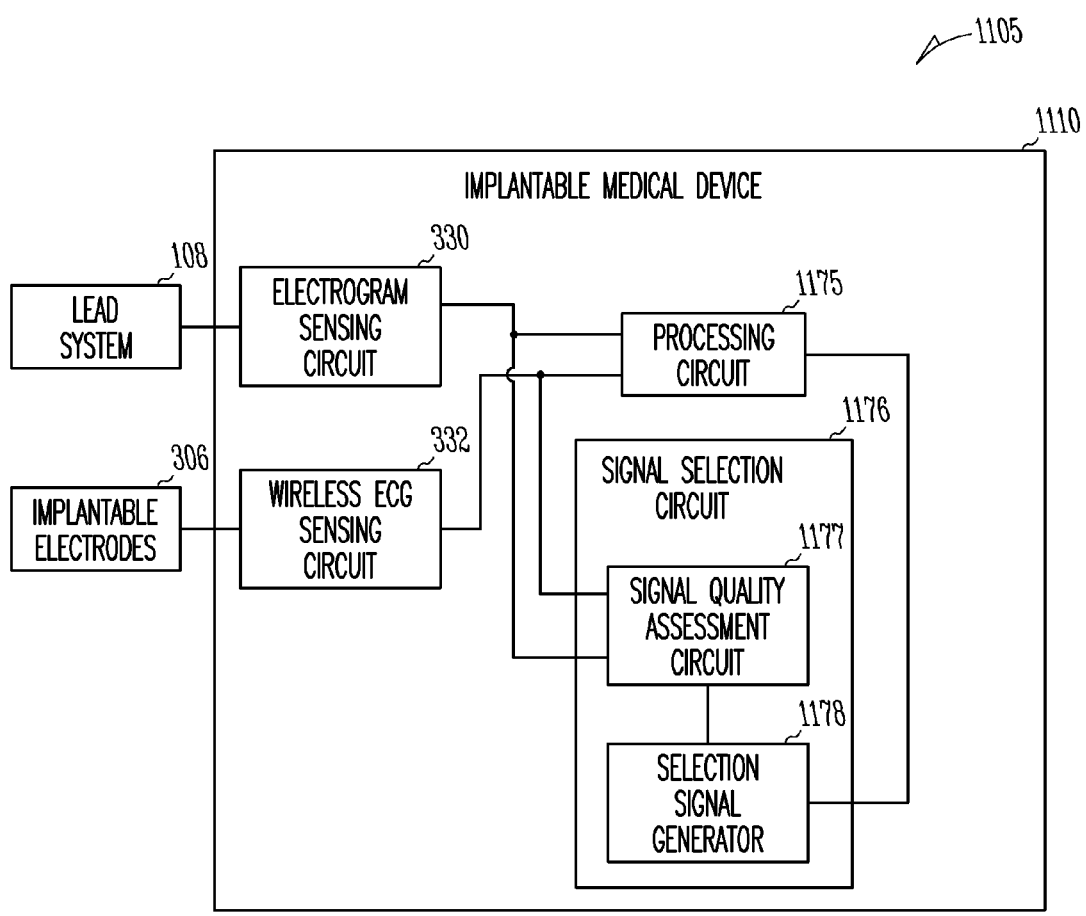
FIG. 11 is a block diagram illustrating an embodiment of portions of an implantable system including a circuit using the wireless ECG as an alternative sensing vector.

FIG. 11 is a block diagram illustrating an embodiment of portions of an implantable system 1105 including a circuit using the wireless ECG as an alternative sensing vector. The circuit includes a sensing circuit to sense a plurality of cardiac signals including one or more intracardiac electrograms and one or more wireless ECGs. At least one cardiac signal of the plurality of cardiac signals is selected for further processing based on the quality or other desirable properties of each cardiac signal. Implantable system 1105 includes lead system 108 for intracardiac electrogram sensing, implantable electrodes 306 for wireless ECG sensing, and an implantable medical device 1110. In one embodiment, implantable system 1105 is part of implantable system 305.

Implantable medical device 1110 includes electrogram sensing circuit 330, wireless ECG sensing circuit 332, processing circuit 1175, and signal selection circuit 1176. Electrogram sensing circuit 330 senses one or more intracardiac electrograms. Wireless ECG sensing circuit 332 senses one or more wireless ECGs. Processing circuit 1175 receives and processes at least one cardiac signal selected from the one or more intracardiac electrograms and the one or more wireless ECGs based on a selection signal produced by signal selection circuit 1176. Signal selection circuit 1176 includes a signal quality assessment circuit 1177 and a selection signal generator 1178. Signal quality assessment circuit 1177 analyzes the one or more intracardiac electrograms and the one or more wireless ECGs and produces quality parameters each being a measure of quality of one of these cardiac signals. Selection signal generator 1178 produces the selection signal based on at least these quality parameters.

Figure 12:
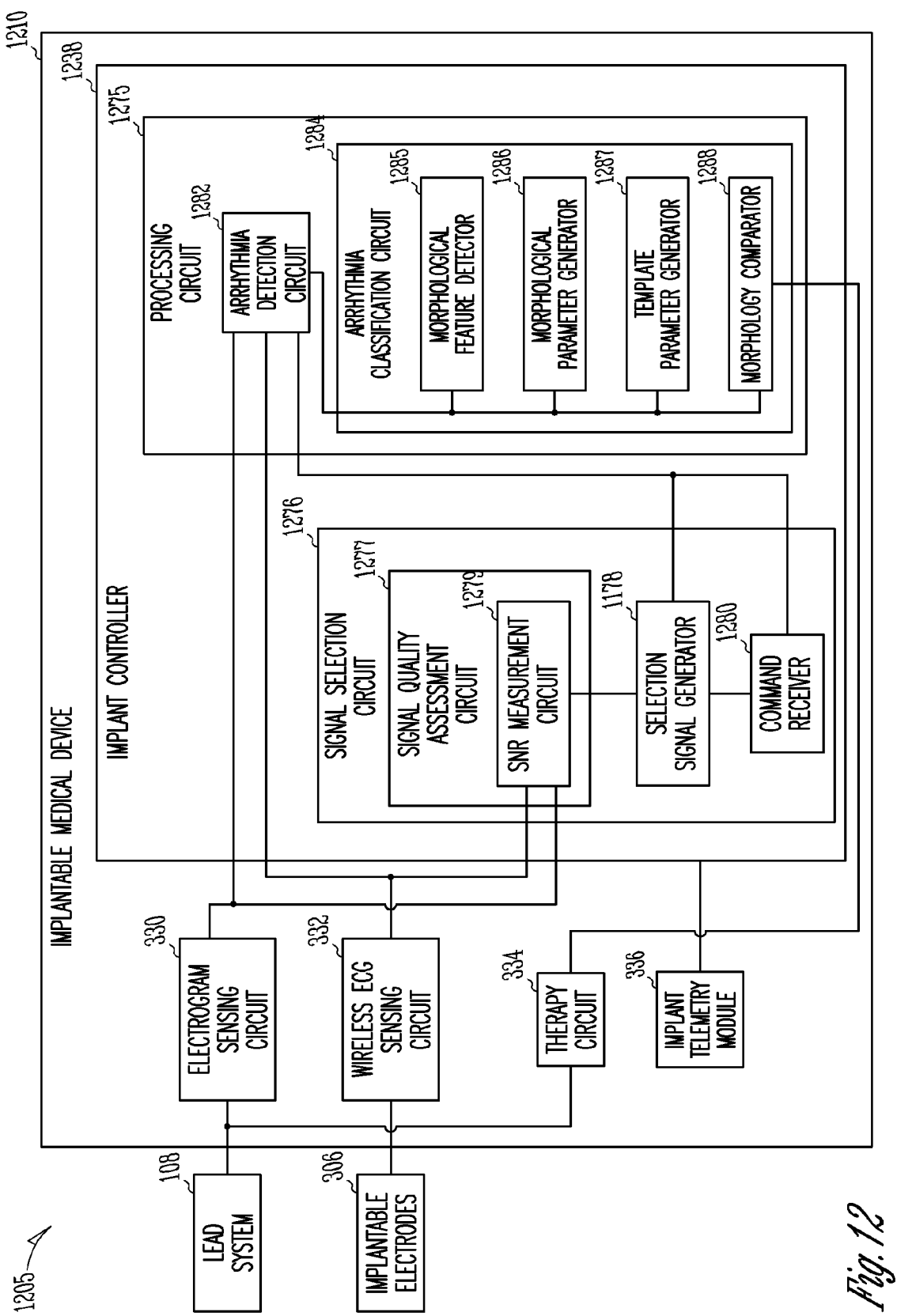
FIG. 12 is a block diagram illustrating an embodiment of portions of another implantable system including the circuit using the wireless ECG as an alternative sensing vector.

FIG. 12 is a block diagram illustrating an embodiment of portions of an implantable system 1205 including the circuit using the wireless ECG as an alternative sensing vector. Implantable system 1205 is a specific embodiment of implantable system 305 and incorporates the general concept, structure, and functions of implantable system 1105 as discussed above. Implantable system 1205 includes lead system 108, implantable electrodes 306, and an implantable medical device 1210. Implantable medical device 1210 is a specific embodiment of implantable medical device 310 and includes electrogram sensing circuit 330, wireless ECG sensing circuit 332, therapy circuit 334, an implant controller 1238, and implant telemetry module 336. In one embodiment, implantable electrodes 306 are incorporated onto implantable medical device 1210 for sensing a subcutaneous ECG as the wireless ECG.

Implant controller 1238 includes a signal selection circuit 1276 being a specific embodiment of signal selection circuit 1176. Signal selection circuit 1276 includes a signal quality assessment circuit 1277, which includes an SNR measurement circuit 1279 to measure an SNR of each of the plurality of cardiac signals including the one or more intracardiac electrograms and the one or more wireless ECGs. Selection signal generator 1178 produces the selection signal based on the SNRs. Command receiver 1280 receives an external command entered by the user. In one embodiment, signal selection circuit 1178 produces the selection signal based on at least the SNRs and the external command. In one specific embodiment, signal selection circuit 1178 produces the selection signal based on at least the SNRs unless directed otherwise by the external command.

In one embodiment, as illustrated in FIG. 12, implant controller 1238 includes a processing circuit 1275 as a specific embodiment of processing circuit 1175. Processing circuit 1275 includes an arrhythmia detection circuit 1282 and an arrhythmia classification circuit 1284. Arrhythmia detection circuit 1282 detects an arrhythmia based on at least one cardiac signal selected from the one or more intracardiac electrograms and the one or more wireless ECGs. Arrhythmia classification circuit 1284 classifies the detected arrhythmia by discriminating between various types of arrhythmias. The discrimination is based on at least one template morphology represented by template parameters, which are measured from morphological features detected from the at least one signal selected from the one or more intracardiac electrograms and the one or more wireless ECGs during a known rhythm. In one embodiment, as illustrated in FIG. 12, arrhythmia classification circuit 1284 includes a morphological feature detector 1285, a morphological parameter generator 1286, a template parameter generator 1287, and a morphology comparator 1288. Morphological feature detector 1285 detects the morphological features. Morphological parameter generator 1286 produces morphological parameters associated with the detected morphological features. Template parameter generator 1287 produces the template parameters. Morphology comparator 1288 classifies the detected arrhythmia by comparing morphological parameters measured from morphological features detected during the detected arrhythmia to the template parameters. In one embodiment, the template parameters are normal sinus rhythm (NSR) template parameters produced based on morphological features detected during an NSR. A detected arrhythmia is classified by discrimination from the NSR. In another embodiment, the template parameters are arrhythmic template parameters produced based on morphological features detected during a known type arrhythmia such as AT or VT. A detected arrhythmia is classified by morphology matching within predetermined windows. In one embodiment, arrhythmia detection circuit 1282 includes an AT detector to detect AT. Arrhythmia classification circuit 1284 classifies the detected AT as AT (i.e., confirms the AT detection) by comparing morphological parameters measured from morphological features detected during the detected AT to predetermined SNR and/or AT template parameters. In another embodiment, arrhythmia detection circuit 1282 includes a VT detector to detect VT. Arrhythmia classification circuit 1284 classifies the detected VT as VT (i.e., confirms the VT detection) by comparing morphological parameters measured from morphological features detected during the detected VT to predetermined SNR and/or VT template parameters. In one embodiment, arrhythmia detection circuit 1282 includes a VT detector to detect VT. Arrhythmia classification circuit 1284 classifies the detected VT as one of VT and SVT based on a comparison between morphological parameters measured from morphological features detected during the detected VT and predetermined VT template parameters.

In one embodiment, arrhythmia detection circuit 1282 includes a VT detector. Arrhythmia classification circuit 1284 classifies each arrhythmia detected by the VT detector as one of VT and a SVT.

It is to be understood that the wireless ECG as an alternative vector can be used for many purposes that require sensing of cardiac activities and that processing circuit 1275 is merely an example illustrating one such use.

Figure 13:
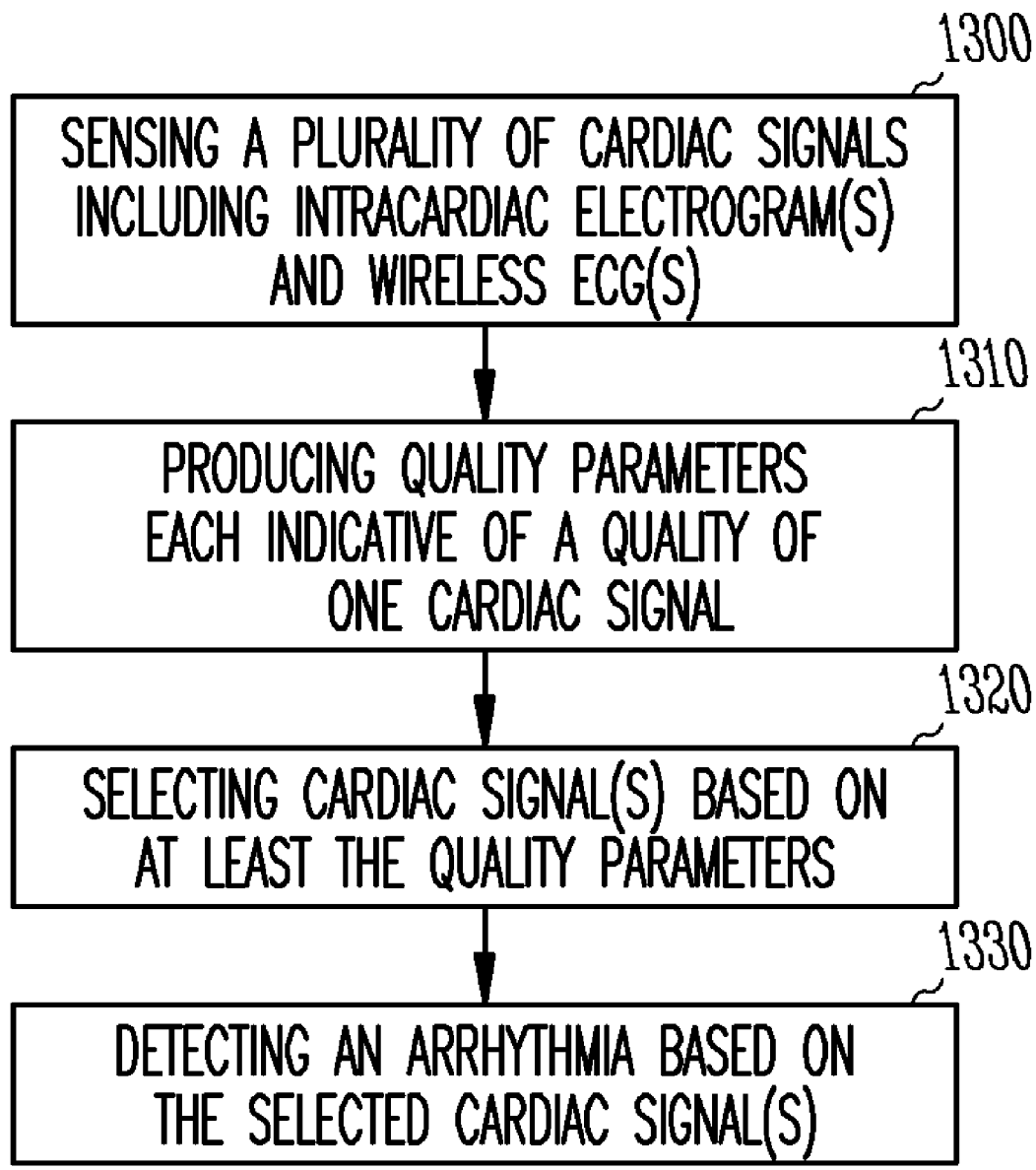
FIG. 13 is a flow chart illustrating an embodiment of a method for using the wireless ECG as an alternative sensing vector.

FIG. 13 is a flow chart illustrating an embodiment of a method for using the wireless ECG as an alternative sensing vector. In one embodiment, the method is performed by a CRM system including implantable system 1105 or implantable system 1205.

A plurality of cardiac signals is sensed at 1300. The plurality of cardiac signals includes one or more intracardiac electrograms and one or more wireless ECGs. Quality parameters each being a measure of quality of one cardiac signal are produced at 1310 based on a quality analysis of the cardiac signals. One or more cardiac signals are selected based on at least the quality parameters at 1320. An arrhythmia is detected based on the selected one or more cardiac signals at 1330.

In one embodiment, the quality parameters include an SNR for each cardiac signal. The SNR for a cardiac signal is measured by using the amplitude of the signal components that are of interest for the intended use as the signal amplitude. For example, if a cardiac signal is to be selected for detecting atrial depolarizations, the SNR is measured by using the amplitude of the P-waves as the signal amplitude.

In one embodiment, an external command is received from the user. At least one cardiac signal is selected based on at least the quality parameters and the user command. In one specific embodiment, the external command has the highest priority in selecting the one or more cardiac signals.

In one embodiment, the detected arrhythmia is classified based on morphological features detected from the selected one or more cardiac signals. The morphological features are detected during the detected arrhythmia. Arrhythmic morphological parameters are produced based on the morphological features detected during the detected arrhythmia. The detected arrhythmia is classified by comparing the arrhythmic morphological parameters to a set of template morphological parameters. The template morphological parameters are produced based on morphological features detected during a known rhythm. In one embodiment, the known rhythm is an NSR. In another embodiment, the known rhythm is a known type arrhythmia. In one embodiment, at least one intracardiac electrogram and at least one wireless ECG are selected, and the template morphological parameters used for the arrhythmia classification are produced based on a combination of at least one intracardiac electrogram and at least one wireless ECG. In one embodiment, the detected arrhythmia is classified as a confirmation of the detection. In one specific embodiment, AT is detected based on an atrial rate and confirmed based on morphological features detected during the detected AT. In another specific embodiment, VT is detected based on a ventricular rate and confirmed based on morphological features detected during the detected VT. In another embodiment, VT is detected based on a ventricular rate and classified as one of VT and SVT based on morphological features detected during the detected VT.

EXAMPLE 4

Detection Confirmation

Figure 14:
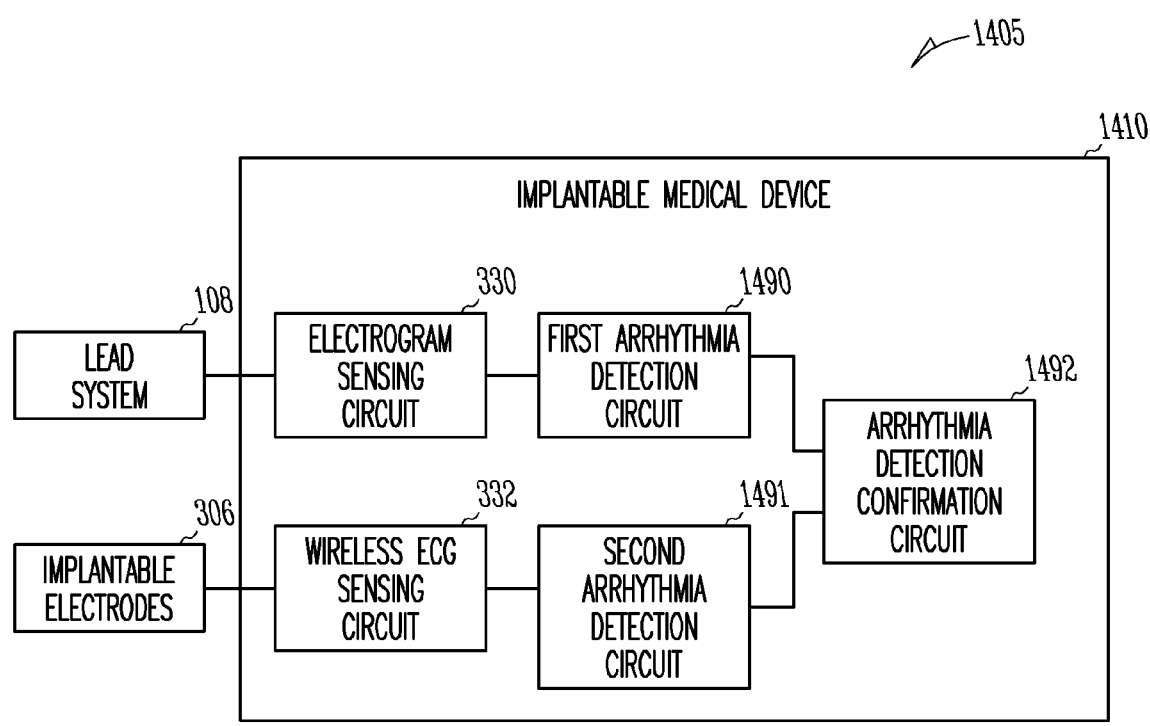
FIG. 14 is a block diagram illustrating an embodiment of portions of an implantable system including a circuit using the wireless ECG to confirm arrhythmia detection.

FIG. 14 is a block diagram illustrating an embodiment of portions of an implantable system 1405 including a circuit using the wireless ECG to confirm arrhythmia detection. Implantable system 1405 includes lead system 108 for intracardiac electrogram sensing, implantable electrodes 306 for wireless ECG sensing, and an implantable medical device 1410. In one embodiment, implantable system 1405 is part of implantable system 305.

Implantable medical device 1410 includes electrogram sensing circuit 330, wireless ECG sensing circuit 332, a first arrhythmia detection circuit 1490, a second arrhythmia detection circuit 1491, and an arrhythmia detection confirmation circuit 1492. First arrhythmia detection circuit 1490 receives an intracardiac electrogram from electrogram sensing circuit 330 and detects an arrhythmia based on the intracardiac electrogram. Second arrhythmia detection circuit 1491 receives a wireless ECG from wireless ECG sensing circuit 332 and detects an arrhythmia based on the wireless ECG. In one embodiment, first arrhythmia detection circuit 1490 and second arrhythmia detection circuit 1491 employ the same arrhythmia detection methodology or substantially similar arrhythmia detection methodologies to detect the same episode of the arrhythmia concurrently. In one specific embodiment, first arrhythmia detection circuit 1490 and second arrhythmia detection circuit 1491 each detect a ventricular arrhythmia by detecting a ventricular rate and compare the detected ventricular rate to a predetermined tachycardia threshold rate. In another embodiment, first arrhythmia detection circuit 1490 and second arrhythmia detection circuit 1491 employ substantially different arrhythmia detection methodologies. Arrhythmia detection confirmation circuit 1492 indicates a detection of an arrhythmia based on the results of detection produced by first arrhythmia detection circuit 1490 and second arrhythmia detection circuit 1491. In one embodiment, arrhythmia detection confirmation circuit 1492 indicates a detection of an arrhythmia only when the same type arrhythmia is detected concurrently by first arrhythmia detection circuit 1490 and second arrhythmia detection circuit 1491. In another embodiment, weighting factors are applied to the results of detection. Arrhythmia detection confirmation circuit 1492 indicates a detection of an arrhythmia based on whether the same type arrhythmia is detected concurrently by first arrhythmia detection circuit 1490 and second arrhythmia detection circuit 1491 as well as the weighting factors. In one embodiment, the weighting factors are produced based on measures of quality of the intracardiac electrogram and the wireless ECG. In one specific embodiment, the weighting factor applied to the result of detection for each arrhythmia detection circuit is determined by the SNR of the signal used by that arrhythmia detection circuit for the detection. The weighting factor increases when the SNR increases. In other embodiments, the weighting factors are determined by the heart rates and/or measures of rate stability for the intracardiac electrogram and the wireless ECG.

In one embodiment, the arrhythmia detection by implantable medical device 1410 includes a classification process. First arrhythmia detection circuit 1490 includes a first arrhythmia classification circuit that classifies the detected arrhythmia based on the intracardiac electrogram. Second arrhythmia detection circuit 1491 includes a second arrhythmia classification circuit that classifies the detected arrhythmia based on the wireless ECG. In one embodiment, the first arrhythmia classification circuit and the second arrhythmia classification circuit employ the same arrhythmia classification methodology or substantially similar arrhythmia classification methodologies to classify the same episode of the arrhythmia concurrently. In another embodiment, the first arrhythmia classification circuit and the second arrhythmia classification circuit employ substantially different arrhythmia classification methodologies. Arrhythmia detection confirmation circuit 1492 includes an arrhythmia classification confirmation circuit to indicate a classification of the arrhythmia based on results of classification produced by the first arrhythmia classification circuit and the second arrhythmia classification circuit. In one embodiment, the arrhythmia classification confirmation circuit indicates a classification of an arrhythmia only when the first arrhythmia classification circuit and the second arrhythmia classification circuit produce consistent classifications. In another embodiment, weighting factors are applied to the results of the classifications produced by the first arrhythmia classification circuit and the second arrhythmia classification circuit. The arrhythmia classification confirmation circuit indicates a classification of an arrhythmia based on whether the first arrhythmia classification circuit and the second arrhythmia classification circuit produce consistent classifications as well as the weighting factors. In one embodiment, the weighting factors used by the arrhythmia classification confirmation circuit are produced based on measures of quality of the intracardiac electrogram and the wireless ECG. In one specific embodiment, the weighting factor applied to the result of detection for each arrhythmia classification circuit is determined by the SNR of the signal used by that arrhythmia classification circuit for the classification. The weighting factor increases when the SNR increases. In other embodiments, the weighting factors are determined by the heart rates and/or measures of rate stability for the intracardiac electrogram and the wireless ECG.

Figure 15:
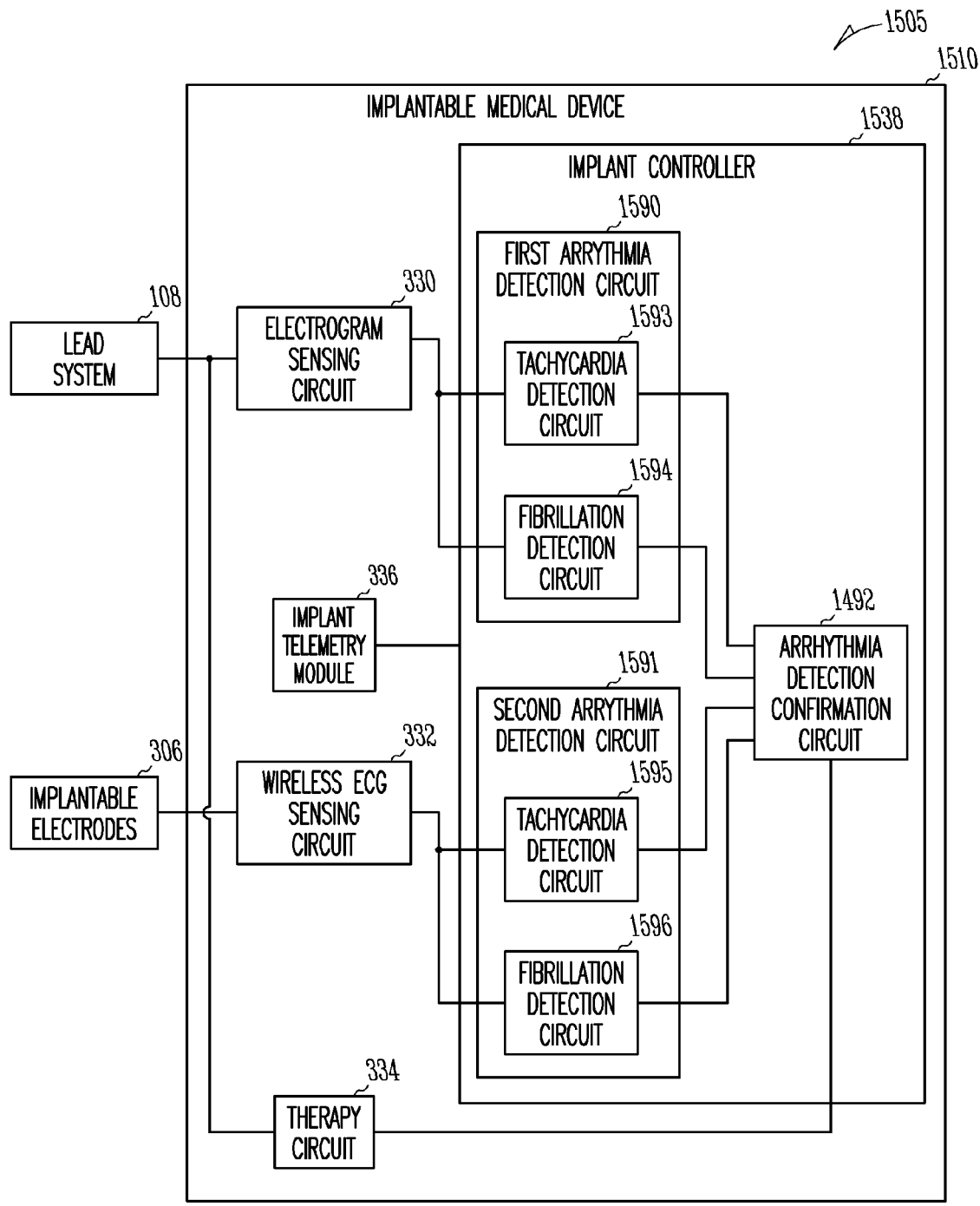
FIG. 15 is a block diagram illustrating an embodiment of portions of another implantable system including the circuit using the wireless ECG to confirm arrhythmia detection.

FIG. 15 is a block diagram illustrating an embodiment of portions of an implantable system 1505 including the circuit using the wireless ECG to confirm arrhythmia detection. Implantable system 1505 is a specific embodiment of implantable system 305 and incorporates the general concept, structure, and functions of implantable system 1405 as discussed above. Implantable system 1505 includes lead system 108, implantable electrodes 306, and an implantable medical device 1510. Implantable medical device 1510 is a specific embodiment of implantable medical device 310 and includes electrogram sensing circuit 330, wireless ECG sensing circuit 332, therapy circuit 334, implant controller 1538, and implant telemetry module 336. In one embodiment, implantable electrodes 306 are incorporated onto implantable medical device 1510 for sensing a subcutaneous ECG as the wireless ECG.

Implant controller 1538 includes a first arrhythmia detection circuit 1590 and a second arrhythmia detection circuit 1591. In one embodiment, electrogram sensing circuit 330 senses an atrial electrogram. Wireless ECG sensing circuit 332 senses a wireless ECG indicative of atrial depolarizations. First arrhythmia detection circuit 1590 and second arrhythmia detection circuit 1591 each detect an atrial arrhythmia including AT and AF. In another embodiment, electrogram sensing circuit 330 senses a ventricular electrogram. Wireless ECG sensing circuit 332 senses a wireless ECG indicative of ventricular depolarizations. First arrhythmia detection circuit 1590 and second arrhythmia detection circuit 1591 each detects a ventricular arrhythmia including VT and VF. First arrhythmia detection circuit 1590 is a specific embodiment of first arrhythmia detection circuit 1490 and includes a tachycardia detection circuit 1593 and a fibrillation detection circuit 1594. Second arrhythmia detection circuit 1591 is a specific embodiment of second arrhythmia detection circuit 1491 and includes a tachycardia detection circuit 1595 and a fibrillation detection circuit 1596. In one embodiment, tachycardia detection circuits 1593 and 1595 are each an AT detector, and fibrillation detection circuits 1594 and 1596 are each an AF detector. In another embodiment, tachycardia detection circuits 1593 and 1595 are each a VT detector, and fibrillation detection circuits 1594 and 1596 are each a VF detector. Arrhythmia detection confirmation circuit 1492 indicates a detection of an arrhythmia when the same type arrhythmia is detected concurrently by first arrhythmia detection circuit 1590 and second arrhythmia detection circuit 1591. Therapy circuit 334 delivers a therapy to the heart when arrhythmia detection confirmation circuit 1492 indicates a detection of an arrhythmia that requires the therapy.

Figure 16:
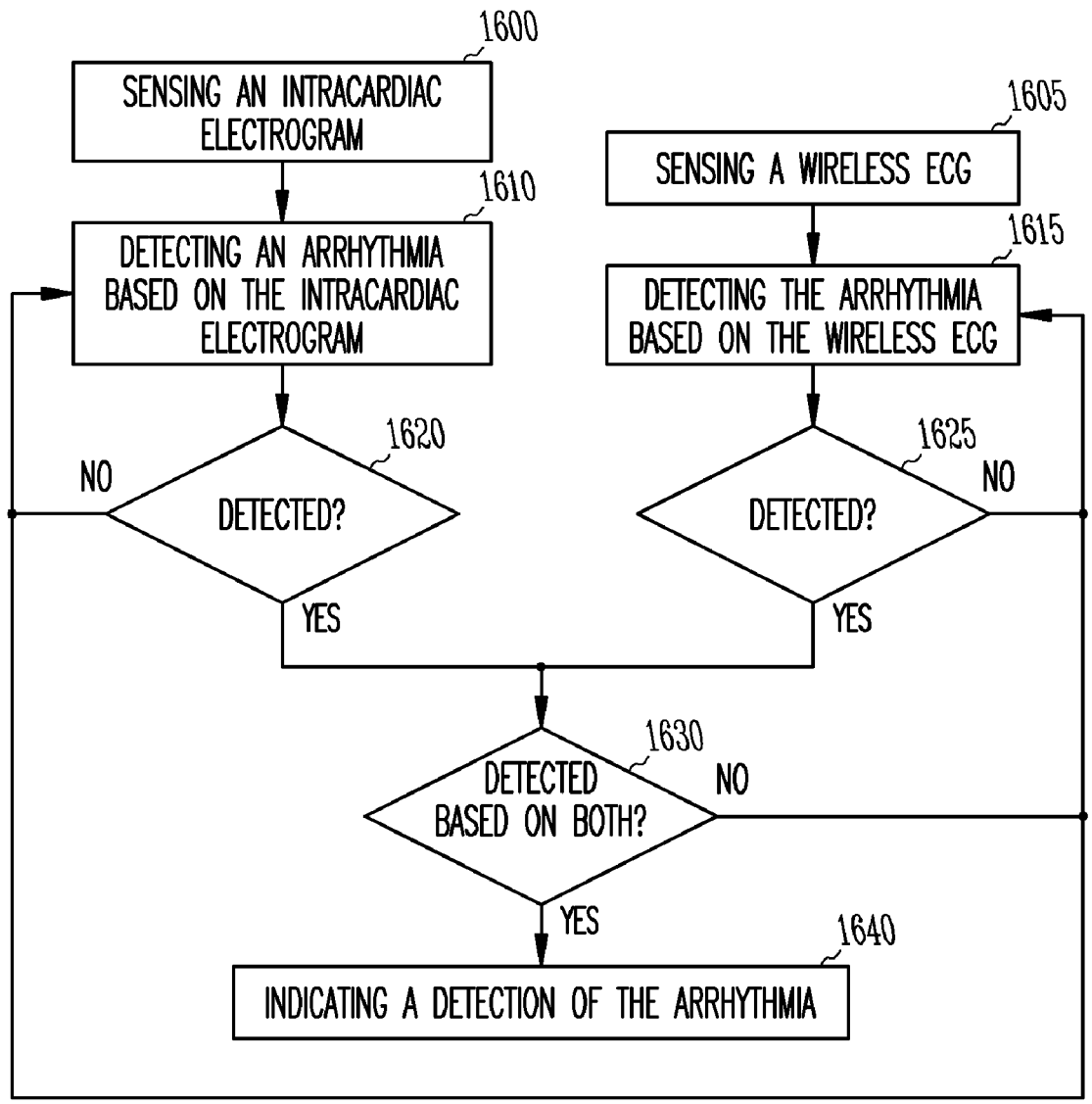
FIG. 16 is a flow chart illustrating an embodiment of a method for using the wireless ECG to confirm arrhythmia detection.

FIG. 16 is a flow chart illustrating an embodiment of a method for using the wireless ECG to confirm arrhythmia detection. In one embodiment, the method is performed by a CRM system including implantable system 1405 or implantable system 1505.

An intracardiac electrogram is sensed at 1600, and arrhythmia is detected based on the intracardiac electrogram at 1610. At the same time, a wireless ECG is sensed at 1605, and arrhythmia is detected based on the wireless ECG at 1615. If an arrhythmia is detected based on the intracardiac electro gram at 1620, it to be confirmed by a concurrent detection of a same-type arrhythmia based on the wireless ECG. If an arrhythmia is detected based on the wireless ECG at 1625, it is to be confirmed based on whether the same type arrhythmia is detected based on the intracardiac electrogram. In one embodiment, if the same type arrhythmia is detected based on the intracardiac electrogram and the wireless ECG concurrently at 1630, a detection of arrhythmia of that type is indicated at 1640. In another embodiment, weighting factors are applied to the results of detecting the arrhythmia based on the subcutaneous ECG and the intracardiac electrogram. In one specific embodiment, the weighting factors are determined based on the SNRs of the intracardiac electro gram and the subcutaneous ECG. In another specific embodiment, the weighting factors are determined based on heart rates measured from the intracardiac electrogram and the subcutaneous ECG. In one embodiment, the intracardiac electrogram is an atrial electrogram, the wireless ECG allows detection of atrial depolarizations, and the arrhythmia to be detected includes AT and AF. In another embodiment, the intracardiac electrogram is a ventricular electro gram, the wireless ECG allows detection of ventricular depolarizations, and the arrhythmia to be detected includes VT and VF.

In one embodiment, the method for using the wireless ECG to confirm arrhythmia detection further includes using the wireless ECG to confirm arrhythmia classification. Arrhythmia is detected and classified based on the intracardiac electrogram at 1610 and concurrently detected and classified based on the wireless ECG at 1615. If an arrhythmia is detected and classified as a particular type arrhythmia based on the intracardiac electrogram at 1620, that classification is to be confirmed by a separate classification based on the wireless ECG. If an arrhythmia is detected and classified as a particular type arrhythmia based on the wireless ECG at 1625, that classification is to be confirmed based on the intracardiac electrogram. In one embodiment, if the same particular type arrhythmia is classified based on the intracardiac electrogram and the wireless ECG concurrently at 1630, a classification of arrhythmia of that particular type is indicated at 1640. In another embodiment, weighting factors are applied to the results of classifying the arrhythmia based on the subcutaneous ECG and the intracardiac electrogram. In one specific embodiment, the weighting factors used for the classification confirmation are determined based on the SNRs of the intracardiac electrogram and the subcutaneous ECG. In another specific embodiment, the weighting factors are determined based on heart rates measured from the intracardiac electrogram and the subcutaneous ECG.

It is to be understood that the above detailed description, including EXAMPLES 1-4, is intended to be illustrative, and not restrictive. For example, the system components of implantable systems 305, 405, 505, 605, 805, 905, 1105, 1205, 1405, and 1505 as discussed above can be combined by various possible permutations to form other implantable systems or devices. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A cardiac rhythm management (CRM) system, comprising:
   a plurality of implantable subcutaneous electrodes; and
   an implantable medical device including:
      a primary sensing circuit including an electrogram sensing circuit to sense an intracardiac electrogram;
      an auxiliary sensing circuit coupled the plurality of implantable subcutaneous electrodes, the auxiliary sensing circuit including a wireless electrocardiogram (ECG) sensing circuit to sense a subcutaneous ECG using the plurality of implantable subcutaneous electrodes;
      a processing circuit having an input to receive a first signal selected from the intracardiac electrogram and the subcutaneous ECG;
      a switch circuit coupled to the input of the processing circuit, the switch circuit configured to receive a selection signal and to connect the input of the processing circuit to the auxiliary sensing circuit such that the subcutaneous ECG is received by the processing circuit as a substitute signal for the intracardiac electrogram in response to the selection signal;
      a selection circuit coupled to the switch circuit, the selection circuit configured to produce the selection signal in response to an indication of a failure mode in which the primary sensing circuit fails to provide reliable sensing of the intracardiac electrogram;
      a hermetically sealed can housing the primary sensing circuit, the auxiliary sensing circuit, the processing circuit, the switch circuit, and the selection circuit; and
      a header attached to the hermetically sealed can,
   wherein the plurality of implantable subcutaneous electrodes are incorporated onto one or both of the hermetically sealed can and the header.

2. The system of claim 1, further comprising at least one lead connected to the primary sensing circuit, the at least one lead including one or more electrodes for sensing the intracardiac electrogram.

3. The system of claim 2, wherein the selection circuit comprises a lead failure detector, coupled to the at least one lead, to detect a lead failure substantially affecting a quality of the intracardiac electrogram, wherein the signal selection circuit produces the selection signal to connect the input of the processing circuit to the auxiliary sensing circuit when the lead failure is detected.

4. The system of claim 3, wherein the lead failure detector comprises a lead impedance measurement circuit.

5. The system of claim 1, wherein the selection circuit comprises a command receiver to receive an external command, wherein the selection circuit produces the selection signal based on the external command.

6. The system of claim 5, further comprising an external system communicatively coupled to the implantable medical device, the external system including a user input to receive the external command.

7. The system of claim 1, wherein the plurality of implantable subcutaneous electrodes comprises one or more header electrodes incorporated into the header.

8. The system of claim 7, wherein the plurality of implantable subcutaneous electrodes comprises a can electrode including at least a conductive portion of the hermetically sealed can.

9. The system of claim 1, wherein the implantable medical device comprises an antenna for telemetry, and wherein the plurality of implantable subcutaneous electrodes comprises an antenna electrode including a portion of the antenna.

10. The system of claim 1, wherein the plurality of implantable subcutaneous electrodes comprises one or more electrodes incorporated onto the hermetically sealed can.

11. The system of claim 10, wherein the plurality of implantable subcutaneous electrodes comprises two or more concentric electrodes incorporated onto the hermetically sealed can.

12. A cardiac rhythm management (CRM) system, comprising:
an implantable medical device including:
a primary sensing circuit including an electrogram sensing circuit to sense an intracardiac electrogram;
an auxiliary sensing circuit including a wireless electrocardiogram (ECG) sensing circuit to sense a subcutaneous ECG;
a processing circuit having an input to receive a first signal being one of the intracardiac electrogram and the subcutaneous ECG;
a switch circuit coupled to the input of the processing circuit, the switch circuit configured to receive a selection signal and to connect the input of the processing circuit to one of the primary sensing circuit and the auxiliary sensing circuit according to the selection signal; and
a selection circuit coupled to the switch circuit, the selection circuit including a signal quality analyzer coupled to the primary sensing circuit, the signal quality analyzer adapted to produce a quality parameter indicative of a quality of the intracardiac electrogram, wherein the selection circuit is adapted to produce the selection signal to connect the input of the processing circuit to the auxiliary sensing circuit when the quality parameter is below a predetermined threshold; and
a plurality of implantable subcutaneous electrodes coupled to the auxiliary sensing circuit.

13. The system of claim 12, wherein the signal quality analyzer comprises a signal-to-noise ratio measurement circuit to measure a signal-to-noise ratio of the intracardiac electrogram.

14. The system of claim 12, wherein the plurality of implantable subcutaneous electrodes comprises at least one electrode incorporated onto the implantable medical device.

15. The system of claim 1, wherein the plurality of implantable subcutaneous electrodes are incorporated onto the implantable medical device.

16. The system of claim 15, wherein the implantable medical device comprises:
a hermetically sealed can housing the primary sensing circuit, the auxiliary sensing circuit, the processing circuit, the switch circuit, and the selection circuit; and
a header attached to the hermetically sealed can,
and wherein the plurality of implantable subcutaneous electrodes comprises one or more header electrodes incorporated into the header.

17. The system of claim 16, wherein the plurality of implantable subcutaneous electrodes comprises a can electrode including at least a conductive portion of the hermetically sealed can.

18. The system of claim 15, wherein the implantable medical device comprises an antenna for telemetry, and wherein the plurality of implantable subcutaneous electrodes comprise an antenna electrode including a portion of the antenna.

19. The system of claim 15, wherein the implantable medical device comprises a hermetically sealed can housing the primary sensing circuit, the auxiliary sensing circuit, the processing circuit, the switch circuit, and the selection circuit, and the plurality of implantable subcutaneous electrodes comprises one or more electrodes incorporated onto the hermetically sealed can.

* * * * *